US011978563B1

(12) United States Patent
Wong et al.

(10) Patent No.: US 11,978,563 B1
(45) Date of Patent: May 7, 2024

(54) SECURE HEALTHCARE COMMUNICATION EXCHANGE PLATFORM

(71) Applicant: Express Scripts Strategic Development, Inc., St. Louis, MO (US)

(72) Inventors: Mark D. Wong, Chesterfield, MO (US); Heather-Ann Falcon, Mahwah, NJ (US); Marian Wilson, Fair Lawn, NJ (US); Jacqueline Luong, Tampa, FL (US); Jared Schutt, Largo, FL (US); Andrew J. Lee, Cypress, TX (US); Ronald Buesser, Boonton Township, NJ (US); Rocco Maglio, Brooksville, FL (US)

(73) Assignee: Express Scripts Strategic Development, Inc., St. Louis, MO (US)

( * ) Notice: Subject to any disclaimer, the term of this patent is extended or adjusted under 35 U.S.C. 154(b) by 201 days.

(21) Appl. No.: 17/126,188

(22) Filed: Dec. 18, 2020

(51) Int. Cl.
*G16H 80/00* (2018.01)
*G16H 10/60* (2018.01)
*G16H 40/67* (2018.01)

(52) U.S. Cl.
CPC .......... *G16H 80/00* (2018.01); *G16H 10/60* (2018.01); *G16H 40/67* (2018.01)

(58) Field of Classification Search
CPC ......... G16H 80/00; G16H 40/67; G16H 10/60
USPC ............................................................ 705/3
See application file for complete search history.

(56) References Cited

U.S. PATENT DOCUMENTS

| | | |
|---|---|---|
| 10,115,167 B2 | 10/2018 | Shen |
| 10,318,960 B2 | 6/2019 | Fitzgerald |
| 10,430,848 B2 | 10/2019 | Cotton |
| 10,748,645 B2 | 8/2020 | Moturu |
| 11,289,208 B1* | 3/2022 | Lippoff .................. G06F 9/547 |
| 2003/0236683 A1* | 12/2003 | Henderson ............ G16H 20/10 705/2 |
| 2004/0220836 A1 | 11/2004 | Doherty |

(Continued)

OTHER PUBLICATIONS

Dixon, B. E., Jabour, A. M., Phillips, E. O. K., & Marrero, D. G. (2014). An informatics approach to medication adherence assessment and improvement using clinical, billing, and patient-entered data. Journal of the American Medical Informatics Association, 21(3), 517-521. (Year: 2014).*

*Primary Examiner* — Mamon Obeid
*Assistant Examiner* — Winston Furtado
(74) *Attorney, Agent, or Firm* — Schwegman Lundberg & Woessner, P.A.

(57) ABSTRACT

Methods and systems for providing a secure healthcare communication exchange platform. The methods and systems perform operations comprising: accessing a collection of data records from a plurality of sources, the collection of data records corresponding to a given entity; generating, based on the collection of data records, an aggregated representation of one or more conditions associated with the given entity; determining, based on the aggregated representation, that a given condition of the one or more conditions satisfies an outreach parameter; in response to determining that the given condition satisfies the outreach parameter, triggering an outreach event to communicate with the given entity; generating status information in the aggregated representation, the status information corresponding to the outreach event; and tracking the status information to establish a relationship between the given condition and the outreach parameter.

20 Claims, 15 Drawing Sheets

(56) References Cited

U.S. PATENT DOCUMENTS

| | | |
|---|---|---|
| 2007/0078680 A1 | 4/2007 | Wennberg |
| 2009/0019516 A1* | 1/2009 | Hammoutene ..... G06F 21/6245 726/1 |
| 2010/0217096 A1* | 8/2010 | Nanikashvili ........ A61B 5/6822 600/301 |
| 2012/0123796 A1 | 5/2012 | McFaul |
| 2014/0279452 A1 | 9/2014 | Hitchmoth |
| 2015/0127380 A1* | 5/2015 | Aaron .................... G16H 10/60 705/3 |
| 2016/0098520 A1 | 4/2016 | Lulias |
| 2017/0061091 A1 | 3/2017 | McElhinney |
| 2017/0061093 A1* | 3/2017 | Amarasingham ...... G16H 10/60 |
| 2018/0315020 A1 | 11/2018 | Shabtai |
| 2019/0297037 A1 | 9/2019 | Peruri |
| 2019/0340654 A1 | 11/2019 | Samotin |
| 2019/0354410 A1* | 11/2019 | Baldasaro ................ G06N 3/08 |
| 2020/0035343 A1* | 1/2020 | Kivatinos .............. G16H 50/70 |

* cited by examiner

SECURE HEALTHCARE COMMUNICATION EXCHANGE PLATFORM — DASHBOARD PATIENTS REFERRALS — INTERNAL USER 1

EXTERNAL USER 1
SUBPOPULATION: NON-ADHERENT> EXTERNAL USER 1

| MEMBER NUMBER: 123344 | | 39 AGE | CLIENT NAME: CLIENT 1 | FEMALE BIOLOGICAL SEX | MEDIUM RISK SCORE | NA ENGAGEMENT SCORE |
|---|---|---|---|---|---|---|
| 05/07/1981 DATE OF BIRTH | | | | | | |

CHANNEL SCORES LETTER: LOW| LIVE CALLS: MEDIUM EMAIL: LOW| AUTOMATED OUTBOUND CALLS: LOW

OUTREACH  OPPORTUNITIES  REFERRALS  MEDICATIONS  CONDITIONS  ALLERGIES  LAB DATA  REMOTE MONITORING

MEDICATIONS

| MEDICATION NAME/ STRENGTH | SUPPLIED AS | Quantity | FILL DATA | LATE TO FILL | DAYS SUPPLY | PATIENT PAID | PRESCRIBER | PHARMACY |
|---|---|---|---|---|---|---|---|---|
| FUROSEMIDE (20MG) | TABLET | 30.000 | 03/25/2019 | 30 | 30 | | EXTERNAL USER 2 | CVS #08190 |
| LISINOPRIL-HYDROCHLORO (20-12.5 MG) | TABLET | 60.000 | 03/25/2019 | 30 | 30 | | NAME: EXTERNAL USER 2 PHONE NUMBER: ADDRESS: ROAD 2, CITY 107, MI 48101 | NAME: CVS#08190 PHONE NUMBER: 1234567894 ADDRESS: ROAD 1, CANTON, MI 48187 |
| GLIMEPIRIDE (2 MG) | TABLET | 60.000 | 01/25/2019 | 30 | 30 | | EXTERNAL USER 2 | CVS #08190 |
| GLIMEPIRIDE (2 MG) | TABLET | 60.000 | 01/25/2019 | 30 | 30 | 4.53 | EXTERNAL USER 2 | CVS #08190 |
| METFORMIN HCL (500 MG) | TABLET | 60.000 | 01/25/2019 | 30 | 30 | 4.53 | EXTERNAL USER 3 | CVS #08190 |
| METFORMIN HCL (500 MG) | TABLET | 60.000 | 01/25/2019 | 30 | 30 | | | |

FIG. 6

SECURE HEALTHCARE COMMUNICATION EXCHANGE PLATFORM

ENROLLMENT | USERS | DASHBOARD | PATIENTS | REFERRALS | INTERNAL USER 1

EXTERNAL USER 1
SUBPOPULATION: NON-ADHERENT>    EXTERNAL USER 1

| MEMBER NUMBER: | 123344 | | CLIENT NAME: | CLIENT 1 | | |
|---|---|---|---|---|---|---|
| 05/07/1981 | 39 | | FEMALE | | MEDIUM | NA |
| DATE OF BIRTH | AGE | | BIOLOGICAL SEX | | RISK SCORE | ENGAGEMENT SCORE |

CHANNEL SCORES LETTER: LOW LIVE CALLS: MEDIUM EMAIL: LOW AUTOMATED OUTBOUND CALLS: LOW

OUTREACH | OPPORTUNITIES | REFERRALS | MEDICATIONS | CONDITIONS | ALLERGIES | LAB DATA | REMOTE MONITORING

LAB DATA

| LAB TEST NAME ◆ | COLLECTION/REPORTING DATE ▼ | LAB RESULTS ◆ | REFERENCE HIGH RANGE ▼ | REFERENCE LOW RANGE ▼ | UNITS ◆ | TEST CODE (LOINC) ◆ | ORDERING PROVIDER ◆ | SERVICING PROVIDER ID |
|---|---|---|---|---|---|---|---|---|
| AMYLASE | 05/01/2018 | 70.000000 | 500.00000 | 3.00000 | un/L | 86888-8 | TMW | 008363872 |
| HEMOGLOBIN (FEMALE) | 05/16/2018 | 11.000000 | 20.00000 | 5.00000 | gm/dL | 11111-1 | ESERVICE DELIVERY(MSD) | 008363916 |
| BUN | 05/01/2018 | 55.000000 | 25.00000 | 5.00000 | mg/dL | 66666-6 | TMW | 008363873 |
| WEIGHT | 04/16/2018 | 800.000000 | 500.00000 | 3.00000 | lb | 44444-4 | TMW | 008359964 |
| CREATININE | 04/16/2018 | 1.000000 | 1.20000 | 0.50000 | mg/dL | 33333-3 | TMW | 008359963 |
| CALCIUM | 04/16/2018 | 10.000000 | 10.50000 | 8.50000 | mg/dL | 22222-2 | TMW | 008359962 |

*FIG. 7*

SECURE HEALTHCARE COMMUNICATION EXCHANGE PLATFORM

DASHBOARD  PATIENTS  REFERRALS

EXTERNAL USER 1  
SUBPOPULATION: NON-ADHERENT

EXTERNAL USER 1

INTERNAL USER 1

| MEMBER NUMBER: | 123344 | | CLIENT NAME: | CLIENT 1 | |
|---|---|---|---|---|---|
| 05/07/1981 DATE OF BIRTH | 39 AGE | | FEMALE BIOLOGICAL SEX | MEDIUM RISK SCORE | NA ENGAGEMENT SCORE |

CHANNEL SCORES LETTER: LOW LIVE CALLS: MEDIUM EMAIL: LOW AUTOMATED OUTBOUND CALLS: LOW

OUTREACH   OPPORTUNITIES   REFERRALS   MEDICATIONS   CONDITIONS   ALLERGIES   LAB DATA   REMOTE MONITORING

OPPORTUNITIES
OPEN   CLOSED

| DESCRIPTION | MEDICATION NAME | GAP DURATION | REMAINING REFILLS | PRIOR CO-PAY | LAST FILL | WRITTEN DATE | PHARMACY | PHARMACY CONTACT NUMBER | DAYS SUPPLY |
|---|---|---|---|---|---|---|---|---|---|
| ADHERENCE WITH RENIN-ANGIOTENSIN SYSTEM ANTAGONIST | LISINOPRIL-HYDROCHLORO | 265 | 3 | 8.39 | 01/22/2019 | 01/22/2019 | CVC #08190 | 1234567894 | 30 |
| ADHERENCE WITH CHOL LOWERING MEDS OT STATINS | GEMFIBROZIL | 262 | 2 | 8.22 | 01/25/2019 | 07/20/2018 | CVC #08190 | 1234567894 | 30 |
| ADHERENCE WITH ORAL INSULIN SECRETAGOGUES | GLIMEPIRIDE | 290 | 2 | 10.19 | 12/28/2018 | 07/20/2018 | CVC #08190 | 1234567894 | 30 |
| ADHERENCE WITH METFORMIN | METFORMIN HCL | 290 | 2 | 0 | 12/28/2018 | 07/20/2018 | CVC #08190 | 1234567894 | 30 |
| DB USE STATINS IN PATIENTS GREATER THAN AGE 75 | GLIMEPIRIDE | 451 | 3 | 10.68 | 07/20/2018 | 07/20/2018 | CVC #08190 | 1234567894 | 30 |

FIG. 8

SECURE HEALTHCARE COMMUNICATION EXCHANGE PLATFORM

ENROLLMENT  USER DASHBOARD  PATIENTS  REFERRALS         INTERNAL USER 2

PATIENT X
PATIENT SEARCH>PATIENT X

| MEMBER NUMBER: 55666 | | CLIENT NAME: CLIENT 2 | | |
|---|---|---|---|---|
| 01/01/2000 DATE OF BIRTH | 20 AGE | FEMALE BIOLOGICAL SEX | NA RISK SCORE | NA ENGAGEMENT SCORE |

CHANNEL SCORES LETTER: NA | LIVE CALLS: NA | EMAIL: NA | AUTOMATED OUTBOUND CALLS: NA

OUTREACH   OPPORTUNITIES   REFERRALS   MEDICATIONS   CONDITIONS   ALLERGIES   LAB DATA   REMOTE MONITORING

CREATE REFERRAL
USER NAME  EXTERNAL USER X
USER ROLE
CLIENT CASE MANAGER
ORGANIZATION
ORGANIZATION MEDICARE

REFERRAL REASON
PATIENT SUPPORT
DESCRIPTION

[ CREATE REFERRAL ]

*FIG. 9*

SECURE HEALTHCARE COMMUNICATION EXCHANGE PLATFORM

INTERNAL USER 1

DASHBOARD  PATIENTS  REFERRALS  ENROLLMENTS  USERS  ADMIN

REFERRALS > REFERRAL SEARCH

REFERRAL SEARCH

NEW    IN PROCESS    COMPLETED    CANCELLED

[EXPORT TO CSV]

| ASSIGNEE | ORGANIZATION | ROLE | PATIENT NAME | MEMBER ID | REASON | DATE |
|---|---|---|---|---|---|---|
| ASHUTOSH | EXPRESS SCRIPTS | SUPER ADMIN | PATIENT 1 | 1234 | PATIENT SUPPORT / PHARMACY SUPPORT / PRACTITIONER SUPPORT | 10/06/2020 |
| ASHUTOSH | EXPRESS SCRIPTS | SUPER ADMIN | PATIENT 1 | 1234 | PATIENT SUPPORT | 10/05/2020 |
| HUB | CLIENT 1 | CLIENT PATIENT CARE - CARE | PATIENT 4 | 566 | PATIENT SUPPORT | 10/05/2020 |
| ASHUTOSH | EXPRESS SCRIPTS | ACADEMIC DETAILER | PATIENT 1 | 1234 | PATIENT SUPPORT | 10/04/2020 |
| ASHUTOSH | EXPRESS SCRIPTS | SUPER ADMIN | PATIENT 1 | 1234 | PATIENT SUPPORT | 10/04/2020 |
| ASHUTOSH | EXPRESS SCRIPTS | SUPER ADMIN | PATIENT 1 | 1234 | PATIENT SUPPORT | 10/03/2020 |

*FIG. 10*

DARRICK EPLER     PATIENT Y
CLINICAL INSIGHTS > SUBPOPULATION : NON-ADHERENT

| MEMBER NUMBER<br>123344 | DATE OF BIRTH<br>01/02/1999 | OVERALL RISK SCORE<br>(MEDIUM) | ENGAGEMENT SCORE<br>(HIGH) |
|---|---|---|---|
| CLIENT NAME<br>CLIENT 1 | AGE<br>21 | | CHANNEL SCORES SHOW |
| PHONE NUMBER<br>(523) 456-7999 | BIOLOGICAL SEX<br>FEMALE | | |

OUTCOMES   OUTREACH OPPORTUNITIES REFERRALS MEDICATIONS CONDITIONS ALLERGIES LAB DATA REMOTE MONITORING

REFERRAL DETAILS
REFERRAL SUMMARY ~1130
[REASSIGN REFERRAL] [COMPLETE REFERRAL] [CANCEL REFERRAL] [REQUEST ITEM] ~1120     [LOG OUTREACH] ~1110

ORIGINAL DETAILS
CREATED BY
INTERNAL USER 1 (SUPER ADMIN)
ASSIGNED TO
CLIENT 1
REFERRAL REASON
PATIENT SUPPORT
CREATED ON
10/06/2020
DESCRIPTION
PATIENT IS SIGNIFICANTLY LTF CITALOPRAM.
PLEASE REACH OUT TO PATIENT TO DISCUSS NON-ADHERENCE.

CURRENT DETAILS
REASSIGNED BY
INTERNAL USER 1 (SUPER ADMIN)
ASSIGNED TO
POPULATION HEALTH MANAGER
REFERRAL REASON
PATIENT SUPPORT
REASSIGNED ON
10-06-2020
DESCRIPTION
PATIENT WOULD BENEFIT FROM AN ADHERENCE DEVICE TO HELP REMEMBER
WHEN SHE NEEDS TO TAKE HER MEDICATION AND A REMOTE MONITORING
DEVICE TO CHECK HER BLOOD PRESSURE READINGS.

[LOG ACTIVITY] [EXPORT TO CSV]

INTERNAL USER 1    SUPER ADMIN                          10/06/2020 03:10:35 PM
REFERRAL REASSIGNED TO POPULATION HEALTH MANAGER
FOR: PATIENT SUPPORT
NOTES: PATIENT WOULD BENEFIT FROM AN ADHERENCE DEVICE TO HELP REMEMBER WHEN SHE NEEDS TO TAKE HER MEDICATION
AND A REMOTE MONITORING DEVICE TO CHECK HER BLOOD PRESSURE READINGS.

INTERNAL USER 1    EXPRESS SCRIPTS - SUPER ADMIN        10/06/2020 03:06:50 PM
REFERRAL CREATED AND ASSIGNED CLIENT 1
FOR: PATIENT SUPPORT
NOTES: PATIENT IS SIGNIFICANTLY LTF CITALOPRAM. PLEASE REACH OUT TO PATIENT TO DISCUSS NON-ADHERENCE.

*FIG. 11*

SECURE HEALTHCARE COMMUNICATION EXCHANGE PLATFORM

BACKGROUND

Modern day healthcare systems are fragmented and complicated. A patient receives a prescription and fills the prescription at a local pharmacy. Once the patient receives their medication, there are very limited resources available to the prescribing physicians and pharmacy to follow up with the patient on their medication. Also, the pharmacy and physician have a very limited and individualized view as to the patient's medications and treatment.

BRIEF DESCRIPTION OF THE DRAWINGS

FIGS. 3-11 are example user interfaces generated by the system of FIG. 1, according to example embodiments.

DETAILED DESCRIPTION

Figure 1:
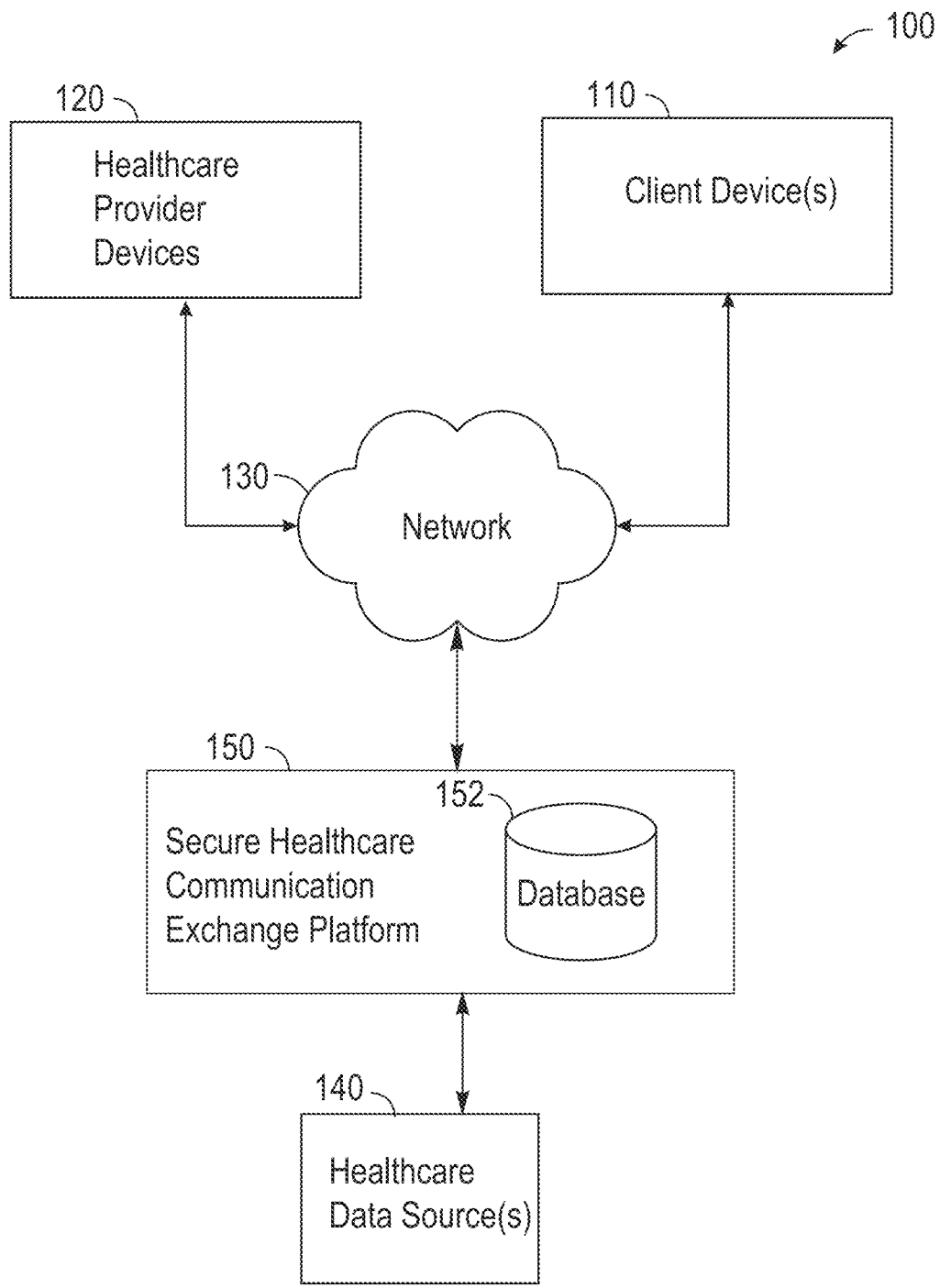
FIG. 1 is a block diagram of an example secure healthcare communication exchange platform system, according to some embodiments.

Example methods and systems for a secure healthcare platform system are described. In the following description, for purposes of explanation, numerous specific details are set forth in order to provide a thorough understanding of example embodiments. It will be evident, however, to one of ordinary skill in the art that embodiments of the invention may be practiced without these specific details.

Healthcare systems allow physicians to prescribe treatment or medication to a patient, or refer a patient for treatment by another care provider. The patient ultimately receives the prescribed treatment or medication from another source. However, there is a lack of coordination and communication of the prescribed treatment or medication the patient receives back to the physician or between caregivers. Also, after dispensing a given drug to a patient, the pharmacy has minimal resources to ensure the patient is adhering to the prescribed medication. Typical healthcare systems lack a common infrastructure that allows the physicians, clinicians, caregivers and pharmacies to have a common holistic view of treatment being received by a particular patient. For example, the pharmacy lacks resources to see what other medications a patient may be receiving and how well or poorly the patient is adhering to or responding to such medication. Because of this, various outreach opportunities to connect with the patients to address issues pertaining to treatment they receive are missed which adversely impacts patient care. The adverse care can be due to the lack of a central repository for communications between healthcare providers, which can ensure that the referral receiving healthcare provider receives a complete referral with all required information fields from the referring healthcare provider and that the referral receiving healthcare provider confirms acceptance of the referral.

Even still, when a pharmacist or physician identifies an outreach opportunity to connect with a given patient, such opportunities are addressed in a way that puts the given patient's secure information at risk. For example, the pharmacist or physician sends an unsecured email or message to someone else or between each other to contact the given patient. The unsecured email or message contains personal and health information associated with the given patient and can potentially be exposed to unauthorized individuals.

Some disclosed embodiments provide a secure healthcare communication exchange platform. The disclosed secure healthcare communication exchange platform allows patient-based referrals to be generated and tracked securely without placing the patient's information at risk of exposure to unauthorized individuals. Patient-based referrals can include a communication coordinating care, such as supplementary care outside of a physician's office, for a particular patient from one entity to another. As an example, the secure healthcare communication exchange platform receives a collection of data about a patient from various external and internal sources, including biometric information, prescription or pharmacy information, medical information and laboratory information. The secure healthcare communication exchange platform can detect that a patient has been recently diagnosed with a given condition and can trigger an outreach event to coordinate additional care to address the given condition.

In an embodiment, the secure healthcare communication exchange platform provides a holistic view of the care being received and provided to a patient and can identify gaps in care that is provided to the patient (e.g., missed doses of a drug, non-adherence to medication, supplementary care that is not being provided, acceptance at a referral receiving caregiver's system and the like). The secure healthcare communication exchange platform can direct or refer another individual, such as a clinician or patient support entity that has access to the secure healthcare communication exchange platform, to communicate with the patient to address the gaps in care. In one example, the secure healthcare communication exchange platform can determine that the collection of data about the patient indicates that the patient has a question about a medication. In response, the secure healthcare communication exchange platform transmits a message or communication to a pharmacist who has access to the secure healthcare communication exchange platform to perform an outreach event, such as contacting the patient to discuss the medication.

In some embodiments, the disclosed methods and systems access a collection of data records from a plurality of sources, the collection of data records corresponding to a given entity and generate, based on the collection of data records, an aggregated representation of one or more conditions associated with the given entity. The disclosed embodiments determine that a given condition of the one or more conditions satisfies an outreach parameter and, in response, trigger an outreach event to communicate with the given entity. The disclosed embodiments generate status information in the aggregated representation corresponding to the outreach event and track the status information to establish a relationship between the given condition and the outreach parameter.

In some embodiments, the presently disclosed systems and methods store a plurality of roles and assign these roles to individuals associated with specific machines or individual machines accesses data in the system related to referrals. The roles have different levels of access to information and communications within the system. This assists with securing the information and the communications. A first role has no access to referral workflow or referral data. A second role is a population health manager, which has access to data relating to patient data and accumulated health data. A third role is an external user that has access to the referral workflow and data relating to referrals. A fourth role is an internal user that has access to the referral workflow and data relating to referrals. A fifth role is a patient care consultant that has access to the referral workflow and data relating to referrals. A fifth role can be a third party vendor that has access to summary data, e.g., overview tables, but not any individual identifying data. The roles can be expanded to include other authorized roles that allow access to patient information and other non-authorized roles that do not allow access to patient information.

FIG. 1 is a block diagram showing an example system 100 according to various exemplary embodiments. The system 100 includes one or more client devices 110, one or more healthcare provider devices 120, a secure healthcare communication exchange platform 150, and one or more healthcare data source(s) that are communicatively coupled over a network 130 (e.g., Internet, telephony network).

As used herein, the term "client device" may refer to any machine that interfaces to a communications network (such as network 130) to access the secure healthcare communication exchange platform 150. The client device 110 may be, but is not limited to, a mobile phone, desktop computer, laptop, portable digital assistants (PDAs), smart phones, a wearable device (e.g., a smart watch), tablets, ultrabooks, netbooks, laptops, multi-processor systems, microprocessor-based or programmable consumer electronics, game consoles, set-top boxes, or any other communication device that a user may use to access a network or the secure healthcare communication exchange platform 150. The client device 110 is a device dedicated to interacting with the secure healthcare communication exchange platform 150 with the client device 110 being loaded with instructions related to the secure healthcare communication exchange platform 150.

In some cases, the secure healthcare communication exchange platform 150 is accessible over a global communication system, e.g., the Internet or world wide web. In such instances, the secure healthcare communication exchange platform 150 hosts a website that is accessible to the client devices 110. Upon accessing the website, the client devices 110 provide secure login credentials, which are used to access a profile associated with the login credentials. One or more user interfaces associated with the secure healthcare communication exchange platform 150 (such as the user interfaces discussed in connection with FIGS. 3-11) are provided over the Internet via the website to the client devices 110.

The client devices 110 may be associated with respective patients. As an example, the client devices 110 may include health monitoring equipment that is connected over the Internet to the secure healthcare communication exchange platform 150. Such health monitoring equipment can include remote blood pressure monitoring devices, glucose monitoring devices, heart monitoring devices, and the like. These health monitoring devices can periodically transmit information that identifies a given patient and provides health related information to the secure healthcare communication exchange platform 150. The secure healthcare communication exchange platform 150 receives such information and stores the information as biometric data associated with the given patient. The client devices 110, when used by a given patient to access the secure healthcare communication exchange platform 150 can view only records that contain information for the particular patient and some but not all portions of the notes associated with the particular patient.

Healthcare provider devices 120 can include the same or similar functionality as client devices 110 for accessing the secure healthcare communication exchange platform 150. In some cases, the healthcare provider devices 120 are used by "internal" users. Internal users are personnel, such as physicians, clinicians, healthcare providers, health-related coaches or the like that are associated with or employed by an organization that provides the secure healthcare communication exchange platform 150. In some cases, the healthcare provider devices 120 are used by "external" users. External users are personnel, such as physicians, clinicians, and health-related coaches that are associated with or employed by a different (external) organization than that which provides the secure healthcare communication exchange platform 150.

The healthcare provider devices 120, when used by internal or external users, to access the secure healthcare communication exchange platform 150 can view many records associated with many different patients. Different levels of authorization can be associated with different internal and different external users to control which records the internal and external users have access. In some instances, only records associated with those patients to which a given internal or external user is referred, are made accessible and available to the given internal or external user device. Sometimes, a first internal or external user can refer a patient or records associated with the patient to a second internal or external user. In such circumstances, the second internal or external user becomes automatically authorized to access and view the patient's records that were referred by the first internal or external user. In an example embodiment, a referral flag can be set in a patient record in the database at the secure healthcare communication exchange platform 150. The referral flag can cause the platform to check an access authorization table that stores access authorization rights to the patient information fields in the database 152.

The network 130 may include, or operate in conjunction with, an ad hoc network, an intranet, an extranet, a virtual private network (VPN), a local area network (LAN), a wireless network, a wireless LAN (WLAN), a wide area network (WAN), a wireless WAN (WWAN), a metropolitan area network (MAN), the Internet, a portion of the Internet, a portion of the Public Switched Telephone Network (PSTN), a plain old telephone service (POTS) network, a cellular telephone network, a wireless network, a Wi-Fi® network, another type of network, or a combination of two or more such networks. For example, a network or a portion of a network may include a wireless or cellular network and the coupling may be a Code Division Multiple Access (CDMA) connection, a Global System for Mobile communications (GSM) connection, or other type of cellular or wireless coupling. In this example, the coupling may implement any of a variety of types of data transfer technology, such as Single Carrier Radio Transmission Technology (1×RTT), Evolution-Data Optimized (EVDO) technology, General Packet Radio Service (GPRS) technology, Enhanced Data rates for GSM Evolution (EDGE) technology, third Generation Partnership Project (3GPP) including 3G, fourth generation wireless (4G) networks, fifth generation wireless (5G) networks, Universal Mobile Telecommunications System (UMTS), High Speed Packet Access (HSPA), Worldwide Interoperability for Microwave Access (WiMAX), Long Term Evolution (LTE) standard, others defined by various standard setting organizations, other long range protocols, or other data transfer technology. The present system can provide secure communications of patient referrals by not freely pushing the patient data out across these communication channels, e.g., email over the public, unencrypted internet. Instead, example embodiments, store the restricted data in the central system and the external devices must log in to pull the data from the central system. The external devices only have access to data relating to projects (e.g., medical referrals, medical counselling, medical procedures and other medical data).

The healthcare data sources 140 provide data records that include healthcare related information for one or more patients. The data records can include multiple hundreds of terabytes of data, which cannot be processed by hand with enough speed for modern healthcare services. The secure healthcare communication exchange platform 150 aggregates the data records received from the healthcare data sources 140 into a collection of data records for each individual patient. Namely, each data record may be tagged with a unique patient identifier (that may or may not include the patient's name). The secure healthcare communication exchange platform 150 collects all the records with the same patient identifier into a single collection associated with the patient. The secure healthcare communication exchange platform 150 stores the collected records in the database 152 as a collection of data records 220. The collection of data records 220 indexes various patient records that have been collected to enable quick and efficient searching and analysis of the patient records.

As an example, one of the healthcare data sources 140 may include pharmacy claims associated with the patent (e.g., the given entity), stored in records. In this case, the secure healthcare communication exchange platform 150 communicates with multiple pharmacies or pharmacy servers to collect pharmacy claims that indicate medication a given patient receives. This way, if the patient fills prescriptions at many different pharmacies, the secure healthcare communication exchange platform 150 can collect all the claims from the various pharmacies into a single location. A clinician or internal or external user can use a healthcare provider device 120 to access the patient record and view all the medications the patient has filled even though they were filled at many different pharmacies. In another implementation, the secure healthcare communication exchange platform 150 communicates with a health insurance carrier associated with the given patient as the healthcare data source 140. The health insurance carrier may securely provide all of the pharmacy related claims that include medication names and doses a given patient was prescribed. The secure healthcare communication exchange platform 150 collects all the medication information into a single record associated with the patient that is made accessible to one or more internal and external users via their respective healthcare provider devices 120.

As another example, one of the healthcare data sources 140 may include medical data associated with the given entity. In this case, the secure healthcare communication exchange platform 150 communicates with multiple physician offices and/or hospitals to collect health services a given patient receives. A clinician, an internal user, or an external user can use a healthcare provider device 120 to access the patient record and view all the health services the patient has received. In another implementation, the secure healthcare communication exchange platform 150 communicates with a health insurance carrier associated with the given patient as the healthcare data source 140. The health insurance carrier may securely provide all of the health services related claims that include physician types or medical services the patient receives (e.g., physical therapy services, hospital visits, and the like). The secure healthcare communication exchange platform 150 collects all the health services information, from various servers, into a single record associated with the patient that is made accessible to one or more internal and external users via their respective healthcare provider devices 120.

As another example, one of the healthcare data sources 140 may include laboratory information associated with the given entity. In this case, the secure healthcare communication exchange platform 150 communicates with multiple laboratory servers to collect laboratory claims that indicate lab results a given patient receives. A clinician or internal or external user can use a healthcare provider device 120 to access the patient record and view all the laboratory results associated with the patient. In another implementation, the secure healthcare communication exchange platform 150 communicates with a health insurance carrier server associated with the given patient as the healthcare data source 140. The health insurance carrier server may securely provide all of the laboratory related claims that include laboratory results for a given patient. The secure healthcare communication exchange platform 150 collects all the laboratory information into a single record associated with the patient that is made accessible to one or more internal and external users via their respective healthcare provider devices 120.

As another example, one of the healthcare data sources 140 or the client devices 110 may include or provide biometric data associated with the given entity. Specifically, the secure healthcare communication exchange platform 150 may receive a first type of biometric data (e.g., blood pressure information) of a given patient directly from the client device 110 associated with the given patient. In such cases, the healthcare data source 140 does not provide the first type of biometric data for the given patient. In another example, the secure healthcare communication exchange platform 150 may receive a second type of biometric data (e.g., blood glucose levels) from the healthcare data source 140 and not from the client device 110. Namely, a given patient may be in possession of a remote blood pressure monitoring devices but may not be in possession of a glucometer. As such, the secure healthcare communication exchange platform 150 receives the first type of biometric data directly from the client device 110 of the patient and receives the second type of biometric data from the healthcare data source 140. In one implementation, the patient visits a site that has a glucometer and that provides the glucometer reading to the healthcare data source 140. The healthcare data source 140 then routes the glucometer reading to the secure healthcare communication exchange platform 150 using a patient identifier of the patient.

The healthcare provider device 120 can be associated with external providers, who can be assigned roles within communication exchange platform 150. The platform 150 can assign external users to rights to access certain data based on a role assigned to that user. Multiple external users may have access to the same or overlapping data for a patient or a patient population. In an example embodiment, external users can assign/reassign to patient health information to other internal users or external users with the data remaining in the platform 150, e.g., in the database 152. In order to assign or reassign the patient health information, the users share a same client population. Internal users are able to assign/re-assign patient health information, e.g., tasks to other internal users or to other external users. The internal users have access to a client population, a book of business or other subgroupings of patient information in order to be assigned or reassigned a patient information or task. Likewise, an internal user assigning or reassign can assign or reassign to an external user, the external user must have access to the client population. Internal users can also intercede and take action on referral regardless if they are the user assign the action or receiving the action. This allows the internal user intercede in a task to keep a task on schedule or correct errors. Additionally, if a task is assigned to an external user who does not take action, the internal user can reassign the task to a new external user or request information from the external user who has not taken action in a timely manner.

Figure 2:
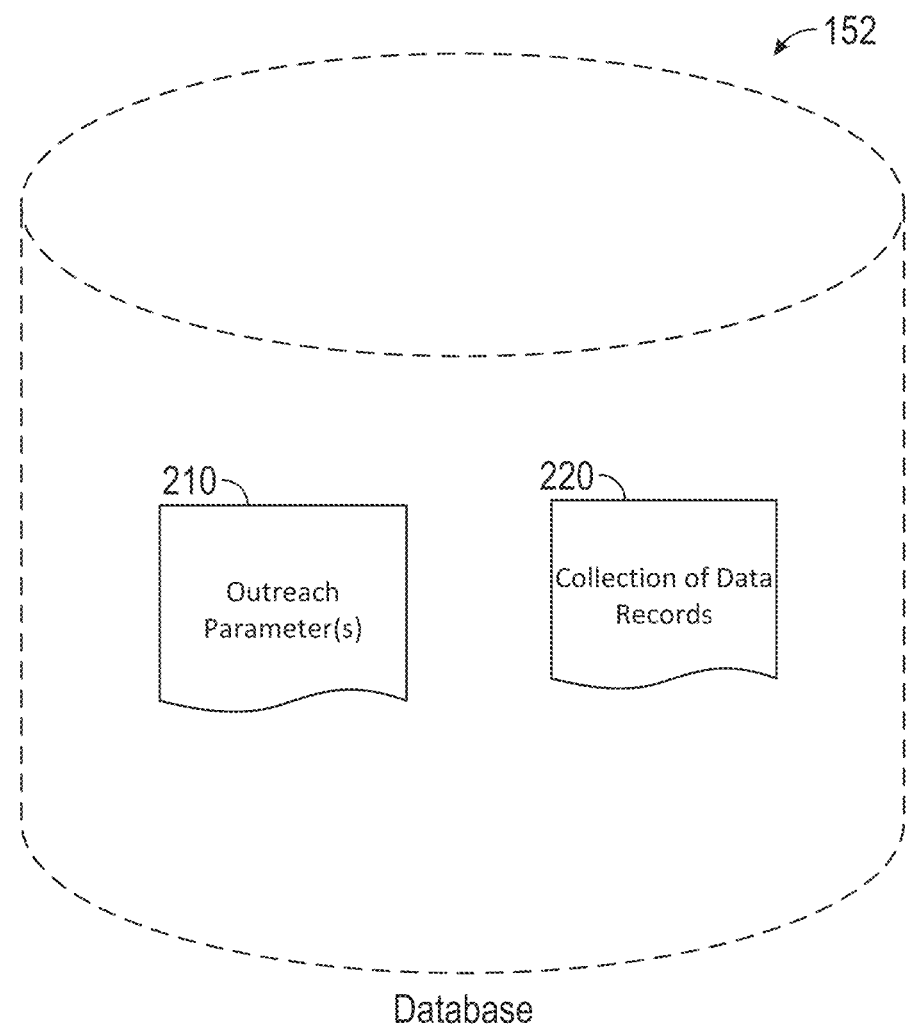
FIG. 2 is an example database that may be deployed within the system of FIG. 1, according to some embodiments.

FIG. 2 is an example database 152 that may be deployed within the system of FIG. 1, according to some embodiments. As shown, the database 152 includes one or more outreach parameter(s) 210 and a collection of data records 220.

The one or more outreach parameter(s) 210 may include criteria that specifies when a given condition or set of conditions of a patient indicate that an outreach to the patient is needed (e.g., an outreach event) to connect with the patient about the conditions. For example, the outreach parameter can include a maximum amount of time allowable for not filling a medication or a threshold amount of late fill period for a given medication or set of medications. The outreach parameter can, additionally or alternatively, include a set of conditions (e.g., patient recently diagnosed with a chronic condition or has recently been discharged from the hospital). When the set of conditions is detected in combination, the outreach parameter is satisfied. The outreach parameter can, additionally or alternatively, include a maximum spend on medications such that when a patient spends more than a threshold amount on the medications, an outreach event is triggered.

In some embodiments, an internal user or an external user can access the secure healthcare communication exchange platform 150 using the healthcare provider device 120 to view one or more patient records. The secure healthcare communication exchange platform 150 can provide an aggregated representation of one or more conditions associated with one or more patients. As an example, the secure healthcare communication exchange platform 150 can present to the internal or external user a graphical user interface shown in FIG. 3. The graphical user interface 300 (which can be output onto a display screen) may be provided after the internal or external user is authenticated by logging in using their respective secure credentials. The user interface 300 allows the internal or external user to select an outreach parameter. For example, the user can select adherence metrics and/or omission of care metrics and/or care optimization metrics. In response to receiving a user selection of an option to view adherence metrics as the outreach parameter, a list of adherence criteria is presented, as shown in user interface 300. In response to receiving a user selection of an option to view care optimization metrics as the outreach parameter, a list of care optimization criteria is presented, as shown in graphical user interface 400 (FIG. 4).

Figure 3:
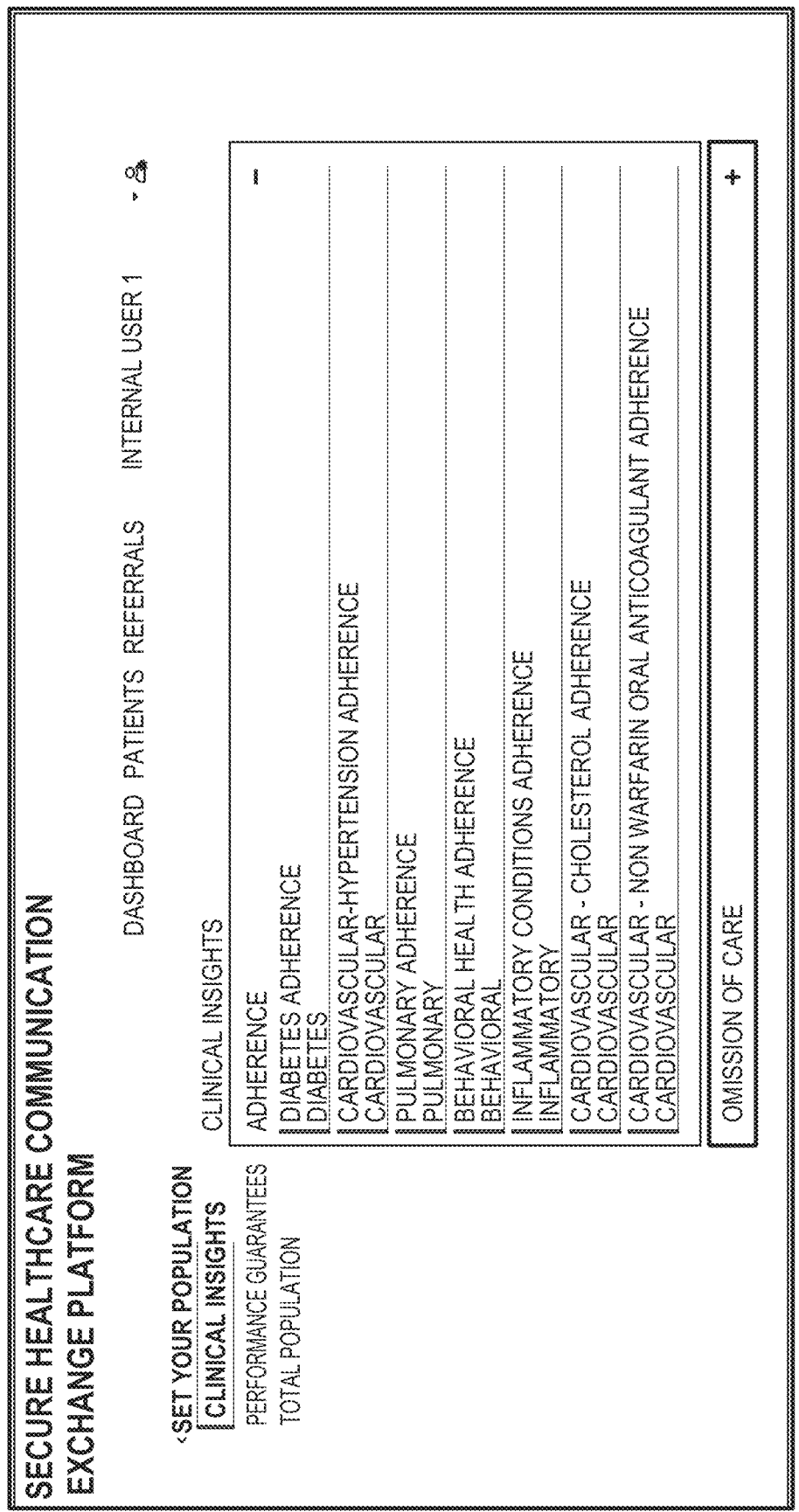
Figure 4:
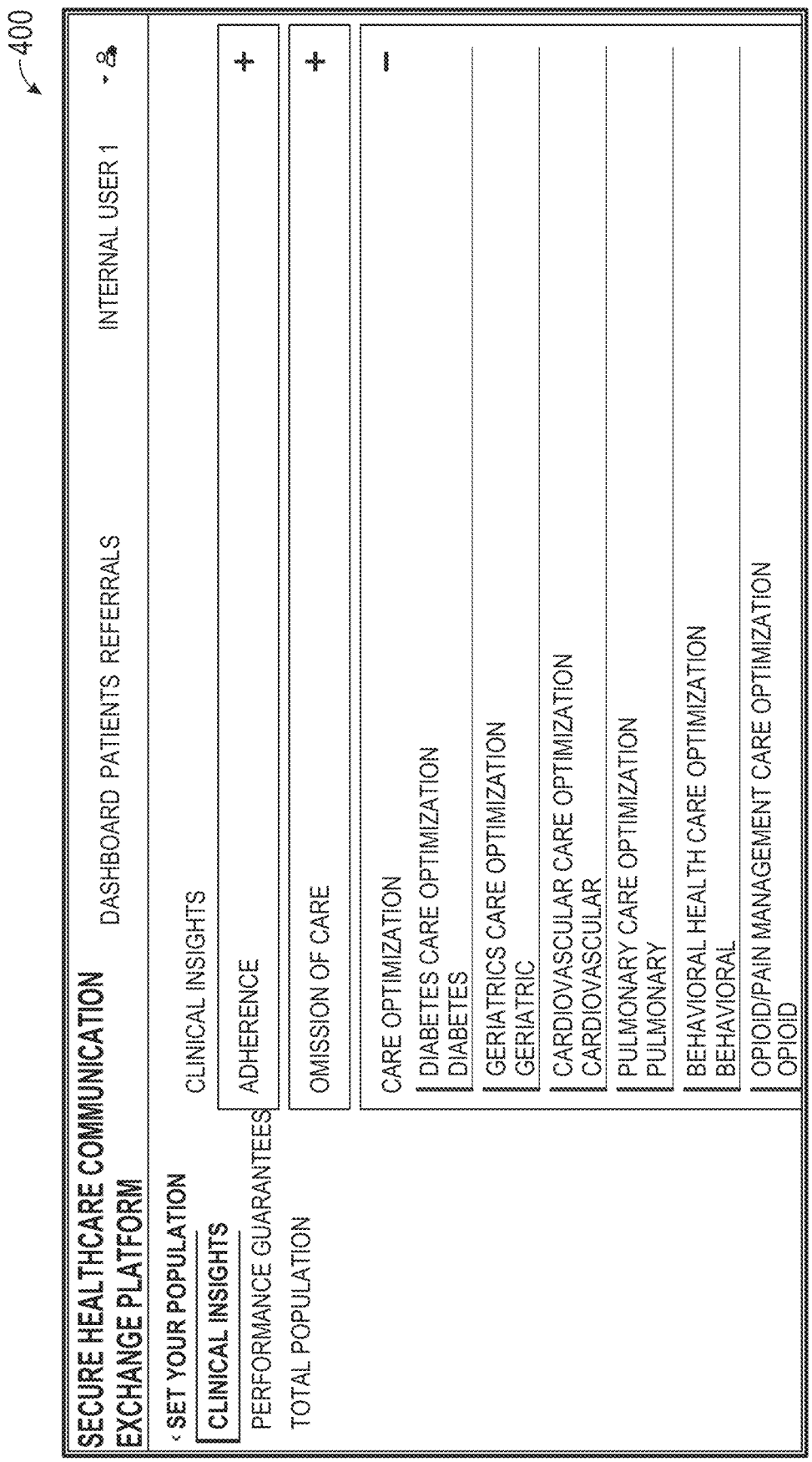
Figure 5:
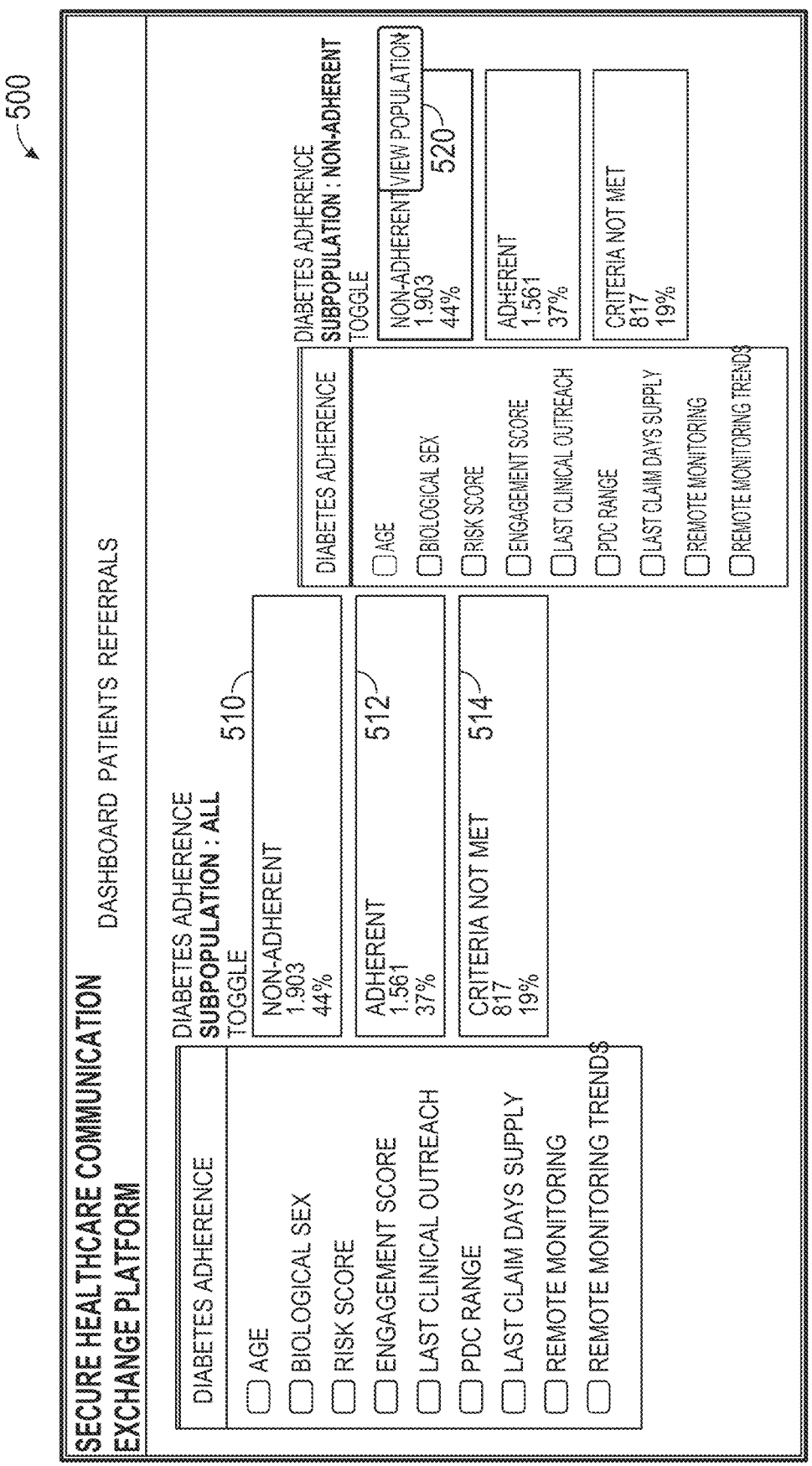

The graphical user interfaces 300, 400 of FIGS. 3 and 4 can be presented to the user on the healthcare provider device 120 of the internal or external user, here shown as internal user 1. The healthcare provider device 120 can receive a user selection of one of the criteria shown in FIG. 3 or 4. As an example, a user input may be received that selects the diabetes adherence criterion of the adherence metrics shown in FIG. 3. In response, a graphical user interface 500 (FIG. 5) is presented to the user on the healthcare provider device 120. Specifically, the secure healthcare communication exchange platform 150 can automatically analyze all of the records stored in the collection of data records 220 to generate a statistical measure of adherence. This statistical measure is provided in the graphical user interface 500. In one example, the secure healthcare communication exchange platform 150 applies one or more trained machine learning models (e.g., a convolutional neural network) to derive relationships between the data stored in the collection of data records 220 to generate predictions as to adherence or other outreach parameters shown in FIG. 3.

The statistical measure can include a first metric 510 representing a quantity or percentage of all patients who are classified as non-adherent to their medications. The statistical measure can include a second metric 512 representing a quantity or percentage of all patients who are classified as being adherent to their medications. The statistical measure can include a third metric 514 representing a quantity or percentage of all patients who have not met the selected diabetes adherence criterion. The user can select one of the statistical measures presented in the user interface 500 to access the population associated with the metric. For example, in response to receiving a user selection of the first metric, a view population option 520 is presented. In response to receiving a user selection of the view population option 520, a list of all patients who were classified as non-adherent can be presented. In some cases, the list of all patients who were classified as non-adherent can be sorted and ranked based on risk categories. Namely, patients who are at greatest risk of having adverse health reactions because they are non-adherent can be automatically identified and presented at the top of the list.

In response to receiving a user selection of a given patient from the presented list, the collection of data records 220 associated with the given patient is retrieved. The collection of data records 220 associated with the given patient is aggregated into a representation shown in graphical user interface 600 (FIG. 6). The user interface 600 includes various regions including a patient information region 610 and a condition related region 620. The patient information region 610 includes a first plurality of fields that identify the given patient (entity). For example, the first plurality of fields includes a patient name, date of birth, age, gender, risk score, and the like. The condition related region 620 includes a second plurality of fields associated with the one or more conditions. The second plurality of field, for example, includes an outreach field, an opportunities field, a referrals field, a medications field, a conditions field, an allergies field, a lab data field, and/or a remote monitoring field. Each field of the second plurality of fields may include data that has been collected from the healthcare data sources 140 and/or from the client device 110 of the given patient or entity.

As an example, input is received that selects the medications field of the second plurality of fields from the condition related region 620. In response, the secure healthcare communication exchange platform 150 obtains a list of medications that the patient is currently prescribed and medications that the patient has been prescribed in the past. Information about each medication is presented that includes a medication name/strength, manner of supply, quantity, fill date, late to fill period, days supply, prescriber identifier and pharmacy identifier. Based on the list of medications, the user can determine that a given condition of the one or more conditions satisfies an outreach parameter. For example, if the late fill period indicating how late the patient was at re-filling the medication exceeds a threshold time period, the user can determine that an outreach parameter is met. In this case, the outreach parameter is a parameter that indicates the patient may be having trouble accessing the pharmacy on time or lacks resources to obtain their prescriptions timely. In some cases, the secure healthcare communication exchange platform 150 automatically highlights or visually identifies a given medication that satisfies an outreach parameter. The user can select the medication to generate a referral request.

As another example, input is received that selects the lab data field of the second plurality of fields from the condition related region 620. In response, the secure healthcare communication exchange platform 150 obtains a list of current and past laboratory results associated with the patient and presents the laboratory results in user interface 700 (FIG. 7). Information about each laboratory result is presented that includes a name of the lab test, a date the lab test was reported or collected, the result of the lab test, a threshold high and low range, a units, a code for the test and the identifier of who ordered the laboratory test. Based on the list of laboratory results, the user can determine that a given condition of the one or more conditions satisfies an outreach parameter. For example, if a threshold number of laboratory tests exceed the maximum (high) range or are below the low or minimum range by more than a threshold amount or value, the user can determine that an outreach parameter is met. In this case, the outreach parameter is a parameter that indicates the patient may be suffering from a chronic condition. In some cases, the secure healthcare communication exchange platform 150 automatically highlights or visually identifies a given one or more laboratory results that satisfy an outreach parameter. The user can select the laboratory results to generate a referral request.

As another example, input is received that selects the opportunities field of the second plurality of fields from the condition related region 620. In response, the secure healthcare communication exchange platform 150 obtains a list of conditions associated with the patient that satisfy one or more outreach parameters and presents such conditions in user interface 800 (FIG. 8). For example, the secure healthcare communication exchange platform 150 can routinely, periodically or continuously process healthcare data associated with patients to detect patterns of behavior or health conditions that can be address with an outreach event (e.g., by communicating with the patient directly about the conditions). Namely, the secure healthcare communication exchange platform 150 can automatically identify medications that have not been re-filled within a threshold amount of time and list such medications among the opportunities presented in user interface 800. The opportunities presented in user interface 800 include a description of the condition (e.g., adherence or lack thereof to a particular medication or other social or economic related condition). As an example, the secure healthcare communication exchange platform 150 can apply various machine learning techniques to the collection of data associated with a given patient to identify an opportunity or condition that satisfies the outreach event. The user can select an opportunity presented in user interface 800 to generate a referral request.

In response to determining that the outreach parameter has been met, the user can start a referral to connect with the given patient. For example, the user can use the healthcare provider device 120 to instruct the secure healthcare communication exchange platform 150 to trigger an outreach event to communicate with the patient. In one example, the secure healthcare communication exchange platform 150 receives a user selection of the referrals field and presents a graphical user interface 900 (FIG. 9) that allows the user to input various information for creating a new referral. Specifically, the user can identify a second internal or external user (e.g., by inputting a particular organization and/or identifier of the second internal or external user). The user can also input one or more reasons for the referral in a description field (e.g., patient support, pharmacy support, practitioner support, healthcare support, pharmaceutical support, need for medicine disposal equipment, need for a remote monitoring device, and the like). Once the user completes the referral, the second internal or external user identified in the referral is notified to act on the outreach event to connect with the patient. The secure healthcare communication exchange platform 150 tracks and maintains the status of the outreach event until the outreach event is closed.

The second internal or external user is provided with authorization to access the aggregated information for the patient identified by the first user. The second user can log into the secure healthcare communication exchange platform 150 via the Internet using the healthcare provider device 120 associated with the second user. In response, the secure healthcare communication exchange platform 150 presents the second user with a full list of pending referrals and their respective status, such as in a graphical user interface 1000 (FIG. 10). For example, graphical user interface 1000 provided by the secure healthcare communication exchange platform 150 presents a total number of pending referrals that have not yet been completed, a total number of completed referrals and a total number of canceled or re-routed referrals. These total numbers are representative of referrals that have been directed to the second user. The total number of canceled referrals represents referrals that the second user has initiated based on analyzing various patient conditions and that the second user has ultimately canceled. The total number of re-routed referrals represents a total number of referrals that the second user has received and has re-directed to an alternate user.

The second user can sort or filter the full list of referrals by who made the referral (e.g., the first user or organization of the first user), reason for the referral (e.g., patient support, pharmacy support, practitioner support, and the like), date, patient name, and/or any combination thereof. The second user can select an option to access the pending referrals. In response, the list of pending referrals including patient names and reasons for the referrals is presented. The second user can sort or filter the pending list of referrals by who made the referral (e.g., the first user or organization of the first user), reason for the referral (e.g., patient support, pharmacy support, practitioner support, and the like), date, patient name, and/or any combination thereof. In response to the secure healthcare communication exchange platform 150 receiving input from the second user that selects a given patient referral, the secure healthcare communication exchange platform 150 presents graphical user interface 1100 (FIG. 11) to the second user.

The user interface 1100 provides various information about the patient and various information about the conditions that led to the referral (e.g., the reasons specified by the first user). The second user can review this information and contact the patient. For example, the second user can call, email, fax, text, or otherwise contact the patient, such as by transmitting a notification to the client device 110 of the patient. Once contact with the patient has been established by the second user, details about the communication with the patient can be entered by the second user into the referral of the aggregated information associated with the patient maintained by the secure healthcare communication exchange platform 150. Specifically, the second user can select a log outreach option 1010. In response, a window is presented that allows the user to enter the time, date and comments received from the patient during the outreach event. In some cases, as a result of the outreach event, the second user can determine that the patient is in need of a health monitoring device. In response, the second user can select a request item option 1120 to select from a list of available health monitoring equipment to send to the patient. Such health monitoring equipment can enable the secure healthcare communication exchange platform 150 to obtain health related information and measurements directly from the patient.

In some cases, the second user can determine that an alternate user is better suited to handle a given referral that has been assigned to the second user. In such circumstances, the second user can select the re-assign referral option 1130. In response, the secure healthcare communication exchange platform 150 allows the second user to specify the identifying information for the alternate internal or external user and the secure healthcare communication exchange platform 150 notifies the selected alternate user to conduct or complete the outreach event. Once the referral has been re-assigned by the second user to the alternate user, access to the given patient's information and data record collection is disabled and the second user becomes de-authorized from accessing the patient record information. Namely, access for the second user becomes disabled preventing the second user from accessing the patient records after the second user re-assigns the referral to the alternate user.

The first user who initiated the referral to the second user can continue to log into the secure healthcare communication exchange platform 150 to access a list of referrals that the first user has made. The secure healthcare communication exchange platform 150 presents to the first user the current status of each referral the first user has made. This allows the first user to continue to track the referrals and their respective status. The first user can also modify or cancel any referral the first user has made. In response to canceling the referral, access previously granted to the second user and/or alternate user is restricted or denied and the referral is added to a list of canceled referrals provided to the first user. The secure healthcare communication exchange platform 150 can also notify the first user when a given referral has been completed (e.g., when an outreach event has been conducted, such as when a log outreach option 1110 has been selected). The secure healthcare communication exchange platform 150 can monitor the patient records overtime, such as after 90 days, to determine whether the same condition that has resulted in the outreach event to be triggered has been resolved. For example, the secure healthcare communication exchange platform 150 can determine whether adherence of the patient to a given medication has increased or whether the patient time for refilling a given medication has been decreased since the outreach even was conducted.

Figure 12:
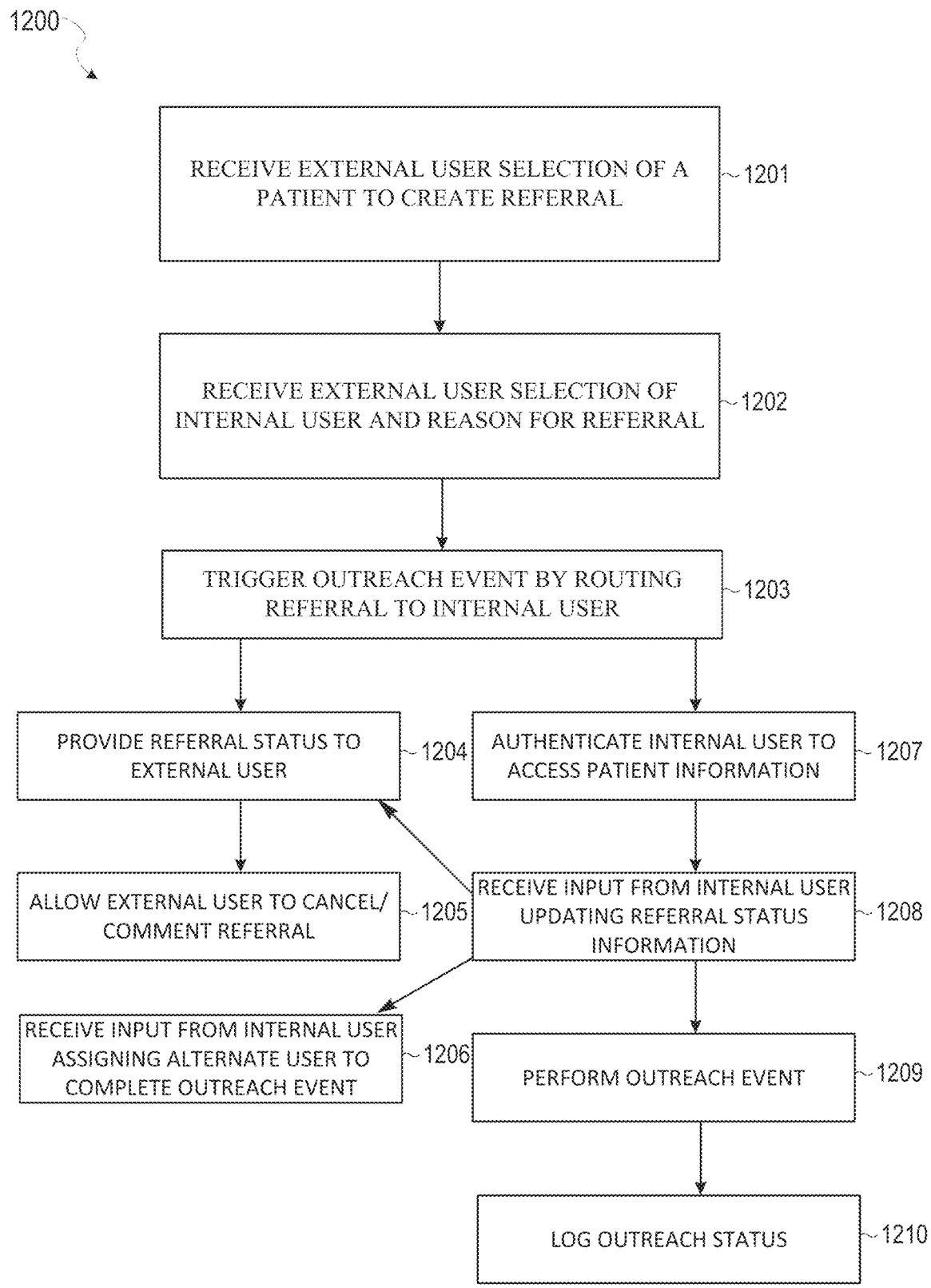
FIG. 12 is a flowchart illustrating example operations of the secure healthcare communication exchange platform, according to example embodiments.

FIG. 12 is a flowchart illustrating example operations of the secure healthcare communication exchange platform in performing process 1200, according to example embodiments. The process 1200 may be embodied in computer-readable instructions for execution by one or more processors such that the operations of the process 1200 may be performed in part or in whole by the functional components of the system 100; accordingly, the process 1200 is described below by way of example with reference thereto. However, in other embodiments, at least some of the operations of the process 1200 may be deployed on various other hardware configurations. Some or all of the operations of process 1200 can be in parallel, out of order, or entirely omitted.

At operation 1201, the secure healthcare communication exchange platform 150 receives an external user selection of a patient to create a referral. For example, the secure healthcare communication exchange platform 150 receives input from a first user that selects a referral request for a given patient.

At operation 1202, the secure healthcare communication exchange platform 150 receives an external user selection of an internal user and a reason for referral. For example, the secure healthcare communication exchange platform 150 presents graphical user interface 900 (FIG. 9) allowing a first user to specify a second user and a reason for referral.

At operation 1203, the secure healthcare communication exchange platform 150 triggers an outreach event by routing the referral to the internal user. For example, the secure healthcare communication exchange platform 150 notifies the second user, such as by adding the referral made by the first user to a list of pending referrals presented to the second user in graphical user interface 1000 (FIG. 10).

At operation 1204, the secure healthcare communication exchange platform 150 provides referral status to the external user. For example, the secure healthcare communication exchange platform 150 allows the first user to log in and view the current status of referrals made by the first user.

At operation 1205, the secure healthcare communication exchange platform 150 allows the external user to cancel/comment on the referral.

At operation 1206, the secure healthcare communication exchange platform 150 receives input from the internal user assigning an alternate user to complete the outreach event. For example, the second user can select an option from user interface 1100 to route the referral to an alternate user.

At operation 1207, the secure healthcare communication exchange platform 150 authenticates or authorizes the internal user to access the patient information. For example, the second user becomes authorized to access the patient records of the patient identified by the first user.

At operation 1208, the secure healthcare communication exchange platform 150 receives input from the internal user updating the referral status information. For example, the second user inputs when and how the patient was contacted and any additional information obtained from the patient during the contact.

At operation 1209, the secure healthcare communication exchange platform 150 performs an outreach event. For example, the second user initiates contact or communication with the patient, such as by phone call, email, text, fax, in person, or otherwise.

At operation 1210, the secure healthcare communication exchange platform 150 logs the outreach status. For example, the second selects a log outreach option in user interface 1100 indicating that contact has been established with the patient.

Figure 13:
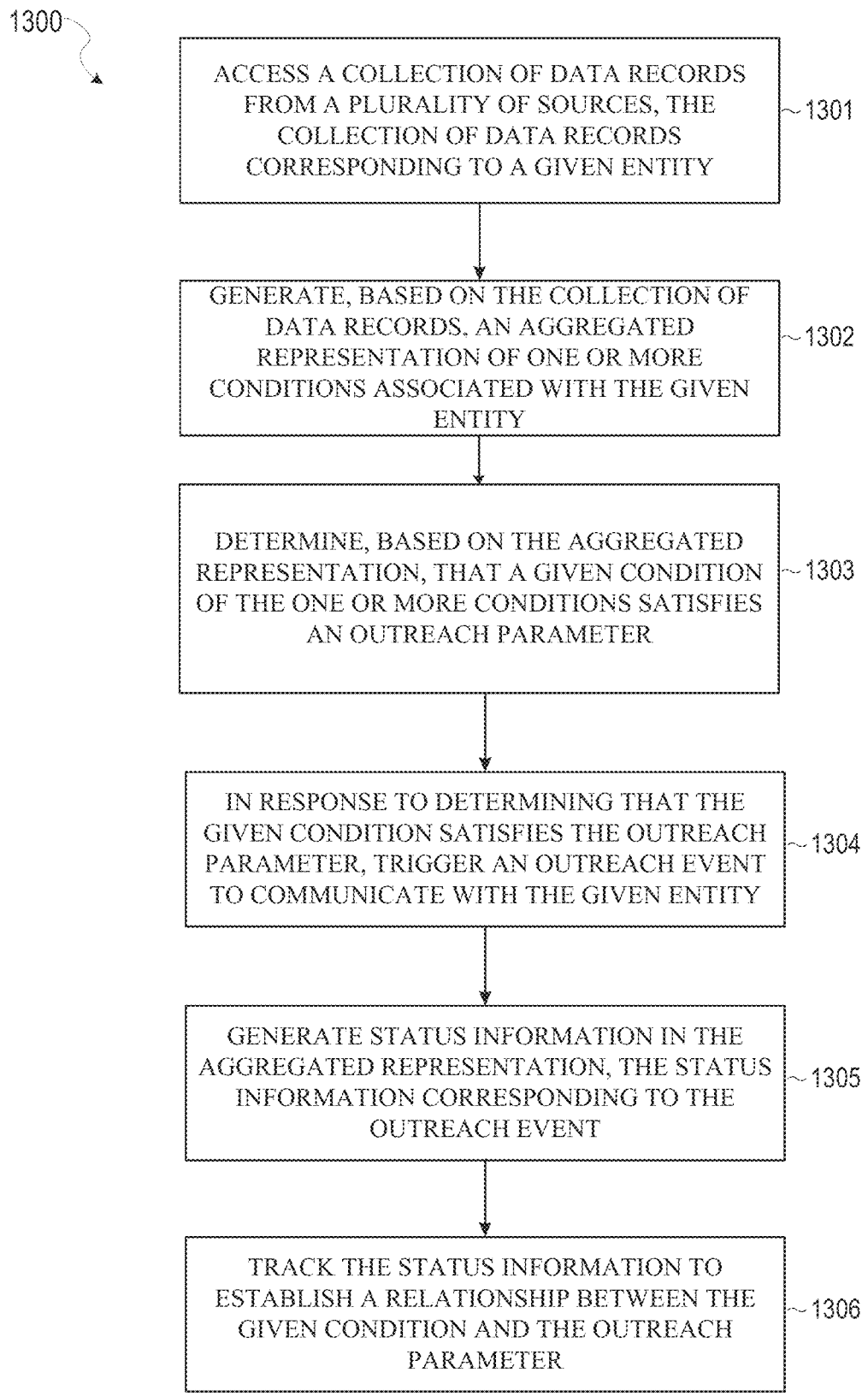
FIG. 13 is a flowchart illustrating example operations of the secure healthcare communication exchange platform, according to example embodiments.

FIG. 13 is a flowchart illustrating example operations of the secure healthcare communication exchange platform in performing process 1300, according to example embodiments. The process 1300 may be embodied in computer-readable instructions for execution by one or more processors such that the operations of the process 1300 may be performed in part or in whole by the functional components of the system 100; accordingly, the process 1300 is described below by way of example with reference thereto. However, in other embodiments, at least some of the operations of the process 1300 may be deployed on various other hardware configurations. Some or all of the operations of process 1300 can be in parallel, out of order, or entirely omitted.

At operation 1301, the secure healthcare communication exchange platform 150 accesses a collection of data records from a plurality of sources that correspond to a given entity. For example, the secure healthcare communication exchange platform 150 accesses data from the healthcare data sources 140 that includes various medical information corresponding to one or more patients (FIG. 1).

At operation 1302, the secure healthcare communication exchange platform 150 generates, based on the collection of data records, an aggregated representation of one or more conditions associated with the given entity. For example, the secure healthcare communication exchange platform 150 aggregates the information received from the sources 140 into a graphical user interface, such as the graphical user interface 600 (FIG. 6) for a given patient.

At operation 1303, the secure healthcare communication exchange platform 150 determines, based on the aggregated representation, that a given condition of the one or more conditions satisfies an outreach parameter. For example, the secure healthcare communication exchange platform 150 identifies medications that are not being filled timely or within a threshold time period.

At operation 1304, the secure healthcare communication exchange platform 150 triggers an outreach event to communicate with the given entity in response to determining that the given condition satisfies the outreach parameter. For example, the secure healthcare communication exchange platform 150 allows an internal or external user to generate a referral, such as via the graphical user interface 900 (FIG. 9).

At operation 1305, the secure healthcare communication exchange platform 150 generates status information in the aggregated representation that corresponds to the outreach event. For example, the internal or external user can access the secure healthcare communication exchange platform 150 to view the current status of referrals, such as whether the patient has been contacted and any comments received from the patient.

At operation 1306, the secure healthcare communication exchange platform 150 tracks the status information to establish a relationship between the given condition and the outreach parameter. For example, the secure healthcare communication exchange platform 150 can determine whether the patient at a later time refills the medication timely.

Figure 14:
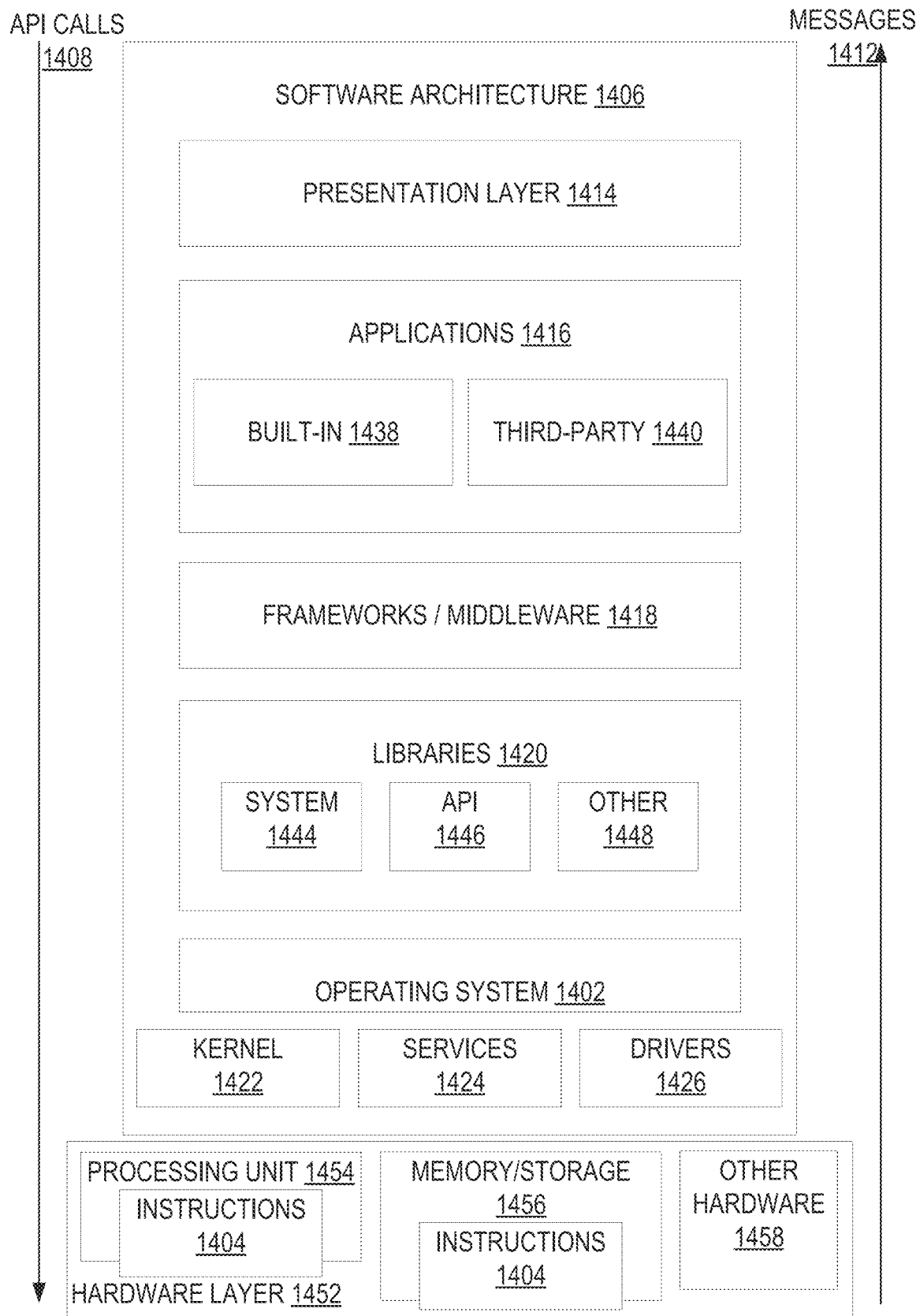
FIG. 14 is a block diagram illustrating an example software architecture, which may be used in conjunction with various hardware architectures herein described.

FIG. 14 is a block diagram illustrating an example software architecture 1406, which may be used in conjunction with various hardware architectures herein described. FIG. 14 is a non-limiting example of a software architecture and it will be appreciated that many other architectures may be implemented to facilitate the functionality described herein. The software architecture 1406 may execute on hardware such as machine 1500 of FIG. 15 that includes, among other things, processors 1504, memory 1514, and input/output (I/O) components 1518. A representative hardware layer 1452 is illustrated and can represent, for example, the machine 1500 of FIG. 15. The representative hardware layer 1452 includes a processing unit 1454 having associated executable instructions 1404. Executable instructions 1404 represent the executable instructions of the software architecture 1406, including implementation of the methods, components, and so forth described herein. The hardware layer 1452 also includes memory and/or storage devices memory/storage 1456, which also have executable instructions 1404. The hardware layer 1452 may also comprise other hardware 1458. The software architecture 1406 may be deployed in any one or more of the components shown in FIG. 1 or 2. The software architecture 1406 can be utilized to aggregate health-related information for many patients and determine whether outreach parameters are satisfied by conditions identified in the health-related information. The software architecture 1406 allows internal or external users to generate and trigger outreach events to contact a patient for which the conditions satisfy the outreach parameters and to track such outreach events.

In the example architecture of FIG. 14, the software architecture 1406 may be conceptualized as a stack of layers where each layer provides particular functionality. For example, the software architecture 1406 may include layers such as an operating system 1402, libraries 1420, frameworks/middleware 1418, applications 1416, and a presentation layer 1414. Operationally, the applications 1416 and/or other components within the layers may invoke API calls 1408 through the software stack and receive messages 1412 in response to the API calls 1408. The layers illustrated are representative in nature and not all software architectures have all layers. For example, some mobile or special purpose operating systems may not provide a frameworks/middleware 1418, while others may provide such a layer. Other software architectures may include additional or different layers.

The operating system 1402 may manage hardware resources and provide common services. The operating system 1402 may include, for example, a kernel 1422, services 1424, and drivers 1426. The kernel 1422 may act as an abstraction layer between the hardware and the other software layers. For example, the kernel 1422 may be responsible for memory management, processor management (e.g., scheduling), component management, networking, security settings, and so on. The services 1424 may provide other common services for the other software layers. The drivers 1426 are responsible for controlling or interfacing with the underlying hardware. For instance, the drivers 1426 include display drivers, camera drivers, Bluetooth® drivers, flash memory drivers, serial communication drivers (e.g., Universal Serial Bus (USB) drivers), Wi-Fi® drivers, audio drivers, power management drivers, and so forth depending on the hardware configuration.

The libraries 1420 provide a common infrastructure that is used by the applications 1416 and/or other components and/or layers. The libraries 1420 provide functionality that allows other software components to perform tasks in an easier fashion than to interface directly with the underlying operating system 1402 functionality (e.g., kernel 1422, services 1424 and/or drivers 1426). The libraries 1420 may include system libraries 1444 (e.g., C standard library) that may provide functions such as memory allocation functions, string manipulation functions, mathematical functions, and the like. In addition, the libraries 1420 may include API libraries 1446 such as media libraries (e.g., libraries to support presentation and manipulation of various media format such as MPREG4, H.264, MP3, AAC, AMR, JPG, PNG), graphics libraries (e.g., an OpenGL framework that may be used to render two-dimensional and three-dimensional in a graphic content on a display), database libraries (e.g., SQLite that may provide various relational database functions), web libraries (e.g., WebKit that may provide web browsing functionality), and the like. The libraries 1420 may also include a wide variety of other libraries 1448 to provide many other APIs to the applications 1416 and other software components/devices.

The frameworks/middleware 1418 (also sometimes referred to as middleware) provide a higher-level common infrastructure that may be used by the applications 1416 and/or other software components/devices. For example, the frameworks/middleware 1418 may provide various graphic user interface functions, high-level resource management, high-level location services, and so forth. The frameworks/middleware 1418 may provide a broad spectrum of other APIs that may be utilized by the applications 1416 and/or other software components/devices, some of which may be specific to a particular operating system 1402 or platform.

The applications 1416 include built-in applications 1438 and/or third-party applications 1440. Examples of representative built-in applications 1438 may include, but are not limited to, a contacts application, a browser application, a book reader application, a location application, a media application, a messaging application, and/or a game application. Third-party applications 1440 may include an application developed using the ANDROID™ or IOS™ software development kit (SDK) by an entity other than the vendor of the particular platform, and may be mobile software running on a mobile operating system such as IOS™, ANDROID™, WINDOWS® Phone, or other mobile operating systems. The third-party applications 1440 may invoke the API calls 1408 provided by the mobile operating system (such as operating system 1402) to facilitate functionality described herein.

The applications 1416 may use built-in operating system functions (e.g., kernel 1422, services 1424, and/or drivers 1426), libraries 1420, and frameworks/middleware 1418 to create UIs to interact with users of the system. Alternatively, or additionally, in some systems, interactions with a user may occur through a presentation layer, such as presentation layer 1414. In these systems, the application/component "logic" can be separated from the aspects of the application/component that interact with a user.

Figure 15:
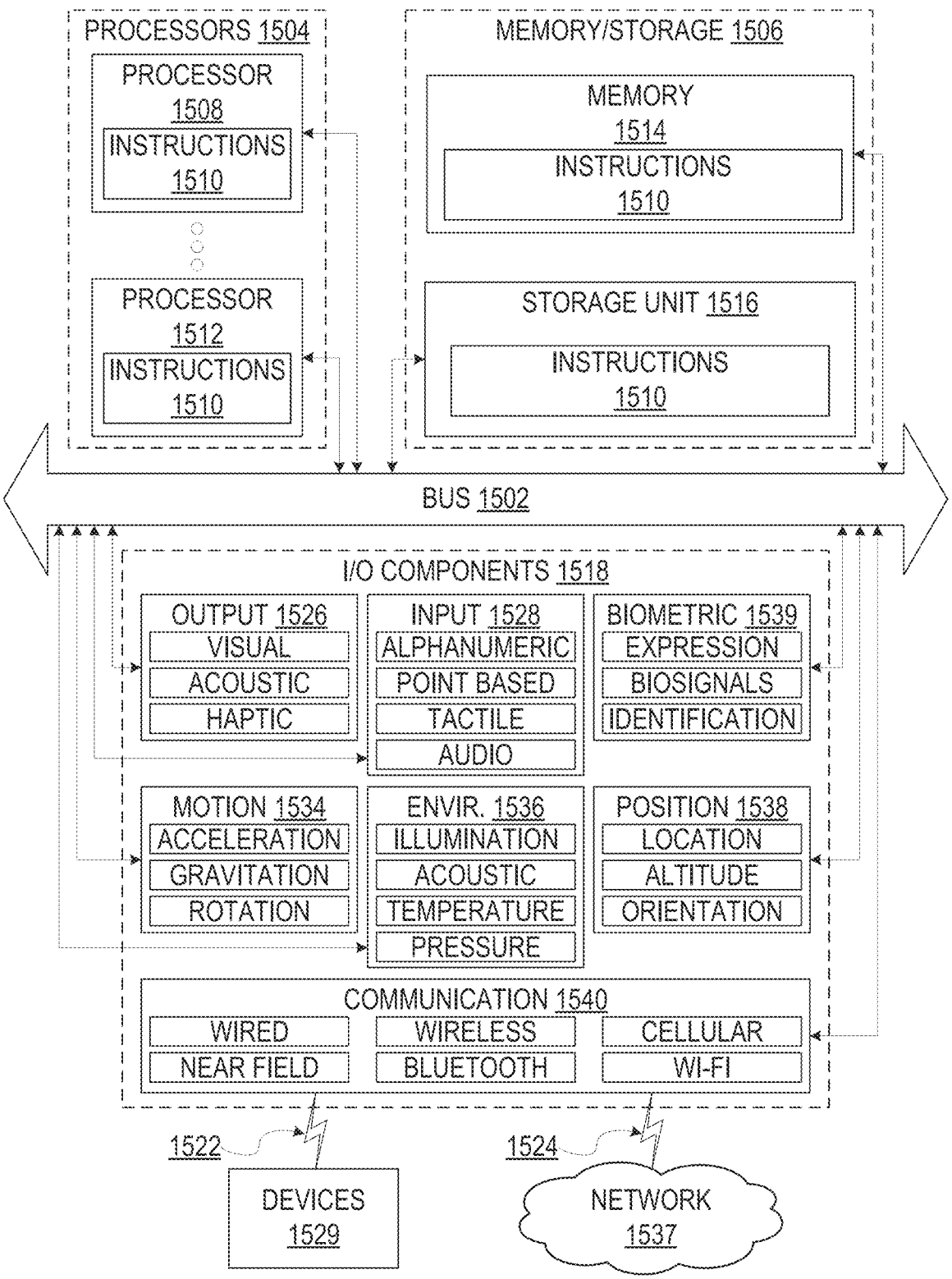
FIG. 15 is a block diagram illustrating components of a machine, according to some example embodiments.

FIG. 15 is a block diagram illustrating components of a machine 1500, according to some example embodiments, able to read instructions from a machine-readable medium (e.g., a machine-readable storage medium) and perform any one or more of the methodologies discussed herein. Specifically, FIG. 15 shows a diagrammatic representation of the machine 1500 in the example form of a computer system, within which instructions 1510 (e.g., software, a program, an application, an applet, an app, or other executable code) for causing the machine 1500 to perform any one or more of the methodologies discussed herein may be executed. For example, the instructions 1510 may be executed by the secure healthcare communication exchange platform 150 to manage and conduct outreach events.

As such, the instructions 1510 may be used to implement devices or components described herein. The instructions 1510 transform the general, non-programmed machine 1500 into a particular machine 1500 programmed to carry out the described and illustrated functions in the manner described. In alternative embodiments, the machine 1500 operates as a standalone device or may be coupled (e.g., networked) to other machines. In a networked deployment, the machine 1500 may operate in the capacity of a server machine or a client machine in a server-client network environment, or as a peer machine in a peer-to-peer (or distributed) network environment. The machine 1500 may comprise, but not be limited to, electronic delivery detection 140, perishable item delivery server 105, smart home service provider server 107, device 132a, device 133a, device 134a, device 132b, device 133b, device 134b, a server computer, a client computer, a personal computer (PC), a tablet computer, a laptop computer, a netbook, a STB, a PDA, an entertainment media system, a cellular telephone, a smart phone, a mobile device, a wearable device (e.g., a smart watch), a smart home device (e.g., a smart appliance), other smart devices, a web appliance, a network router, a network switch, a network bridge, or any machine capable of executing the instructions 1510, sequentially or otherwise, that specify actions to be taken by machine 1500. Further, while only a single machine 1500 is illustrated, the term "machine" shall also be taken to include a collection of machines that individually or jointly execute the instructions 1510 to perform any one or more of the methodologies discussed herein. When the instructions 1510 are loaded, the machine 1500 is a dedicated machine for performing the processes described herein.

The machine 1500 may include processors 1504, memory/storage 1506, and I/O components 1518, which may be configured to communicate with each other such as via a bus 1502. In an example embodiment, the processors 1504 (e.g., a central processing unit (CPU), a reduced instruction set computing (RISC) processor, a complex instruction set computing (CISC) processor, a graphics processing unit (GPU), a digital signal processor (DSP), an application-specific integrated circuit (ASIC), a radio-frequency integrated circuit (RFIC), another processor, or any suitable combination thereof) may include, for example, a processor 1508 and a processor 1512 that may execute the instructions 1510. The term "processor" is intended to include multi-core processors 1504 that may comprise two or more independent processors (sometimes referred to as "cores") that may execute instructions contemporaneously. Although FIG. 15 shows multiple processors 1504, the machine 1500 may include a single processor with a single core, a single processor with multiple cores (e.g., a multi-core processor), multiple processors with a single core, multiple processors with multiple cores, or any combination thereof.

The memory/storage 1506 may include a memory 1514, such as a main memory, or other memory storage, database 110, and a storage unit 1516, both accessible to the processors 1504 such as via the bus 1502. The storage unit 1516 and memory 1514 store the instructions 1510 embodying any one or more of the methodologies or functions described herein. The instructions 1510 may also reside, completely or partially, within the memory 1514, within the storage unit 1516, within at least one of the processors 1504 (e.g., within the processor's cache memory), or any suitable combination thereof, during execution thereof by the machine 1500. Accordingly, the memory 1514, the storage unit 1516, and the memory of processors 1504 are examples of machine-readable media.

The I/O components 1518 may include a wide variety of components to receive input, provide output, produce output, transmit information, exchange information, capture measurements, and so on, such as devices 132a-b, 133a-b, and 134a-b. The specific I/O components 1518 that are included in a particular machine 1500 will depend on the type of machine. For example, portable machines such as mobile phones will likely include a touch input device or other such input mechanisms, while a headless server machine will likely not include such a touch input device. It will be appreciated that the I/O components 1518 may include many other components that are not shown in FIG. 15. The I/O components 1518 are grouped according to functionality merely for simplifying the following discussion and the grouping is in no way limiting. In various example embodiments, the I/O components 1518 may include output components 1526 and input components 1528. The output components 1526 may include visual components (e.g., a display such as a plasma display panel (PDP), a light emitting diode (LED) display, a liquid crystal display (LCD), a projector, or a cathode ray tube (CRT)), acoustic components (e.g., speakers), haptic components (e.g., a vibratory motor, resistance mechanisms), other signal generators, and so forth. The input components 1528 may include alphanumeric input components (e.g., a keyboard, a touch screen configured to receive alphanumeric input, a photo-optical keyboard, or other alphanumeric input components), point-based input components (e.g., a mouse, a touchpad, a trackball, a joystick, a motion sensor, or other pointing instrument), tactile input components (e.g., a physical button, a touch screen that provides location and/or force of touches or touch gestures, or other tactile input components), audio input components (e.g., a microphone), and the like.

In further example embodiments, the I/O components 1518 may include biometric components 1539, motion components 1534, environmental components 1536, or position components 1538 among a wide array of other components. For example, the biometric components 1539 may include components to detect expressions (e.g., hand expressions, facial expressions, vocal expressions, body gestures, or eye tracking), measure biosignals (e.g., blood pressure, heart rate, body temperature, perspiration, or brain waves), identify a person (e.g., voice identification, retinal identification, facial identification, fingerprint identification, or electroencephalogram based identification), and the like. The motion components 1534 may include acceleration sensor components (e.g., accelerometer), gravitation sensor components, rotation sensor components (e.g., gyroscope), and so forth. The environmental components 1536 may include, for example, illumination sensor components (e.g., photometer), temperature sensor components (e.g., one or more thermometer that detect ambient temperature), humidity sensor components, pressure sensor components (e.g., barometer), acoustic sensor components (e.g., one or more microphones that detect background noise), proximity sensor components (e.g., infrared sensors that detect nearby objects), gas sensors (e.g., gas detection sensors to detection concentrations of hazardous gases for safety or to measure pollutants in the atmosphere), or other components that may provide indications, measurements, or signals corresponding to a surrounding physical environment. The position components 1538 may include location sensor components (e.g., a GPS receiver component), altitude sensor components (e.g., altimeters or barometers that detect air pressure from which altitude may be derived), orientation sensor components (e.g., magnetometers), and the like.

Communication may be implemented using a wide variety of technologies. The I/O components 1518 may include communication components 1540 operable to couple the machine 1500 to a network 1537 or devices 1529 via coupling 1524 and coupling 1522, respectively. For example, the communication components 1540 may include a network interface component or other suitable device to interface with the network 1537. In further examples, communication components 1540 may include wired communication components, wireless communication components, cellular communication components, Near Field Communication (NFC) components, Bluetooth® components (e.g., Bluetooth® Low Energy), Wi-Fi® components, and other communication components to provide communication via other modalities. The devices 1529 may be another machine or any of a wide variety of peripheral devices (e.g., a peripheral device coupled via a USB).

Moreover, the communication components 1540 may detect identifiers or include components operable to detect identifiers. For example, the communication components 1540 may include Radio Frequency Identification (RFID) tag reader components, NFC smart tag detection components, optical reader components (e.g., an optical sensor to detect one-dimensional bar codes such as Universal Product Code (UPC) bar code, multi-dimensional bar codes such as Quick Response (QR) code, Aztec code, Data Matrix, Dataglyph, MaxiCode, PDF417, Ultra Code, UCC RSS-2D bar code, and other optical codes), or acoustic detection components (e.g., microphones to identify tagged audio signals). In addition, a variety of information may be derived via the communication components 1540, such as location via Internet Protocol (IP) geo-location, location via Wi-Fi® signal triangulation, location via detecting a NFC beacon signal that may indicate a particular location, and so forth.

Glossary:

"CARRIER SIGNAL" in this context refers to any intangible medium that is capable of storing, encoding, or carrying transitory or non-transitory instructions for execution by the machine, and includes digital or analog communications signals or other intangible medium to facilitate communication of such instructions. Instructions may be transmitted or received over the network using a transitory or non-transitory transmission medium via a network interface device and using any one of a number of well-known transfer protocols.

"CLIENT DEVICE" in this context refers to any machine that interfaces to a communications network to obtain resources from one or more server systems or other client devices. A client device may be, but is not limited to, a mobile phone, desktop computer, laptop, PDA, smart phone, tablet, ultra book, netbook, laptop, multi-processor system, microprocessor-based or programmable consumer electronics, game console, set-top box, or any other communication device that a user may use to access a network.

"COMMUNICATIONS NETWORK" in this context refers to one or more portions of a network that may be an ad hoc network, an intranet, an extranet, a virtual private network (VPN), a LAN, a wireless LAN (WLAN), a wide area network (WAN), a wireless WAN (WWAN), a metropolitan area network (MAN), the Internet, a portion of the Internet, a portion of the Public Switched Telephone Network (PSTN), a plain old telephone service (POTS) network, a cellular telephone network, a wireless network, a Wi-Fi® network, another type of network, or a combination of two or more such networks. For example, a network or a portion of a network may include a wireless or cellular network and the coupling may be a Code Division Multiple Access (CDMA) connection, a Global System for Mobile communications (GSM) connection, or other type of cellular or wireless coupling. In this example, the coupling may implement any of a variety of types of data transfer technology, such as Single Carrier Radio Transmission Technology (1xRTT), Evolution-Data Optimized (EVDO) technology, General Packet Radio Service (GPRS) technology, Enhanced Data rates for GSM Evolution (EDGE) technology, third Generation Partnership Project (3GPP) including 3G, fourth generation wireless (4G) networks, Universal Mobile Telecommunications System (UMTS), High Speed Packet Access (HSPA), Worldwide Interoperability for Microwave Access (WiMAX), Long Term Evolution (LTE) standard, others defined by various standard setting organizations, other long range protocols, or other data transfer technology.

"MACHINE-READABLE MEDIUM" in this context refers to a component, device, or other tangible media able to store instructions and data temporarily or permanently and may include, but is not limited to, random-access memory (RAM), read-only memory (ROM), buffer memory, flash memory, optical media, magnetic media, cache memory, other types of storage (e.g., Erasable Programmable Read-Only Memory (EEPROM)) and/or any suitable combination thereof. The term "machine-readable medium" should be taken to include a single medium or multiple media (e.g., a centralized or distributed database, or associated caches and servers) able to store instructions. The term "machine-readable medium" shall also be taken to include any medium, or combination of multiple media, that is capable of storing instructions (e.g., code) for execution by a machine, such that the instructions, when executed by one or more processors of the machine, cause the machine to perform any one or more of the methodologies described herein. Accordingly, a "machine-readable medium" refers to a single storage apparatus or device, as well as "cloud-based" storage systems or storage networks that include multiple storage apparatus or devices. The term "machine-readable medium" excludes signals per se.

"COMPONENT" in this context refers to a device, physical entity, or logic having boundaries defined by function or subroutine calls, branch points, APIs, or other technologies that provide for the partitioning or modularization of particular processing or control functions. Components may be combined via their interfaces with other components to carry out a machine process. A component may be a packaged functional hardware unit designed for use with other components and a part of a program that usually performs a particular function of related functions. Components may constitute either software components (e.g., code embodied on a machine-readable medium) or hardware components. A "hardware component" is a tangible unit capable of performing certain operations and may be configured or arranged in a certain physical manner. In various example embodiments, one or more computer systems (e.g., a stand-alone computer system, a client computer system, or a server computer system) or one or more hardware components of a computer system (e.g., a processor or a group of processors) may be configured by software (e.g., an application or application portion) as a hardware component that operates to perform certain operations as described herein.

A hardware component may also be implemented mechanically, electronically, or any suitable combination thereof. For example, a hardware component may include dedicated circuitry or logic that is permanently configured to perform certain operations. A hardware component may be a special-purpose processor, such as a Field-Programmable Gate Array (FPGA) or an ASIC. A hardware component may also include programmable logic or circuitry that is temporarily configured by software to perform certain operations. For example, a hardware component may include software executed by a general-purpose processor or other programmable processor. Once configured by such software, hardware components become specific machines (or specific components of a machine) uniquely tailored to perform the configured functions and are no longer general-purpose processors. It will be appreciated that the decision to implement a hardware component mechanically, in dedicated and permanently configured circuitry, or in temporarily configured circuitry (e.g., configured by software) may be driven by cost and time considerations. Accordingly, the phrase "hardware component" (or "hardware-implemented component") should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware components are temporarily configured (e.g., programmed), each of the hardware components need not be configured or instantiated at any one instance in time. For example, where a hardware component comprises a general-purpose processor configured by software to become a special-purpose processor, the general-purpose processor may be configured as respectively different special-purpose processors (e.g., comprising different hardware components) at different times. Software accordingly configures a particular processor or processors, for example, to constitute a particular hardware component at one instance of time and to constitute a different hardware component at a different instance of time.

Hardware components can provide information to, and receive information from, other hardware components. Accordingly, the described hardware components may be regarded as being communicatively coupled. Where multiple hardware components exist contemporaneously, communications may be achieved through signal transmission (e.g., over appropriate circuits and buses) between or among two or more of the hardware components. In embodiments in which multiple hardware components are configured or instantiated at different times, communications between such hardware components may be achieved, for example, through the storage and retrieval of information in memory structures to which the multiple hardware components have access. For example, one hardware component may perform an operation and store the output of that operation in a memory device to which it is communicatively coupled. A further hardware component may then, at a later time, access the memory device to retrieve and process the stored output.

Hardware components may also initiate communications with input or output devices and can operate on a resource (e.g., a collection of information). The various operations of example methods described herein may be performed, at least partially, by one or more processors that are temporarily configured (e.g., by software) or permanently configured to perform the relevant operations. Whether temporarily or permanently configured, such processors may constitute processor-implemented components that operate to perform one or more operations or functions described herein. As used herein, "processor-implemented component" refers to a hardware component implemented using one or more processors. Similarly, the methods described herein may be at least partially processor-implemented, with a particular processor or processors being an example of hardware. For example, at least some of the operations of a method may be performed by one or more processors or processor-implemented components. Moreover, the one or more processors may also operate to support performance of the relevant operations in a "cloud computing" environment or as a "software as a service" (SaaS). For example, at least some of the operations may be performed by a group of computers (as examples of machines including processors), with these operations being accessible via a network (e.g., the Internet) and via one or more appropriate interfaces (e.g., an API). The performance of certain of the operations may be distributed among the processors, not only residing within a single machine, but deployed across a number of machines. In some example embodiments, the processors or processor-implemented components may be located in a single geographic location (e.g., within a home environment, an office environment, or a server farm). In other example embodiments, the processors or processor-implemented components may be distributed across a number of geographic locations.

"PROCESSOR" in this context refers to any circuit or virtual circuit (a physical circuit emulated by logic executing on an actual processor) that manipulates data values according to control signals (e.g., "commands," "op codes," "machine code," etc.) and which produces corresponding output signals that are applied to operate a machine. A processor may, for example, be a CPU, a RISC processor, a CISC processor, a GPU, a DSP, an ASIC, a RFIC, or any combination thereof. A processor may further be a multi-core processor having two or more independent processors (sometimes referred to as "cores") that may execute instructions contemporaneously.

"TIMESTAMP" in this context refers to a sequence of characters or encoded information identifying when a certain event occurred, for example giving date and time of day, sometimes accurate to a small fraction of a second.

Changes and modifications may be made to the disclosed embodiments without departing from the scope of the present disclosure. These and other changes or modifications are intended to be included within the scope of the present disclosure, as expressed in the following claims.

The Abstract of the Disclosure is provided to comply with 37 C.F.R. § 1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter may lie in less than all features of a single disclosed embodiment. Thus, the following claims are hereby incorporated into the Detailed Description, with each claim standing on its own as a separate embodiment.

What is claimed is:

1. A method comprising:
    accessing, by one or more processors of a secure healthcare communication exchange platform, a collection of data records from a plurality of data sources, the collection of data records corresponding to a patient user;
    modifying each data record in the collection of data records, the modification comprising tagging each data record with a unique identifier value;
    generating, based on the unique identifier value associated with each record in the collection of data records, an aggregate data record associated with the patient user;
    receiving a first selection from a graphical user interface of a first computer device, the first selection corresponding to an adherence metric associated with the aggregate data record;
    in response to the first selection, analyzing the adherence metric using a convolutional neural network trained to generate a prediction on a statistical measure of adherence of the adherence metric;
    based on the generated prediction, automatically identifying, using a machine learning technique, a subset of data records of the aggregate data record that satisfies an outreach parameter, the machine learning technique trained to analyze the aggregate data record;
    in response to determining that the subset of data records satisfy the outreach parameter, receiving a second selection from a graphical user interface by the first computer device, the first selection triggering an outreach event to authorize a second computer device to access the aggregate data record, wherein the first computer device user has a viewing-level access authorizing the first computer device to view the aggregate data record, and the second computer device has a restricted-level access that restricts the second computer device from viewing the aggregate data record;
    in response to triggering the outreach event, automatically modifying, without user intervention the restricted-level access associated with the second computer device to the viewing-level access, the second computer device user becoming authorized to view the aggregate data record; and
    in response to the second computer device becoming authorized to view the aggregate data record, initiating contact through the secure healthcare communication exchange platform with the patient user so that a health condition associated with the patient user is resolved and the aggregate data record associated with the patient user is exposed only to an authorized user.

2. The method of claim 1, further comprising:
    storing the collection of records corresponding to the patient user on the secure healthcare communication exchange platform.

3. The method of claim 1, wherein the plurality of data sources comprises pharmacy claims associated with the patient user, medical data associated with the patient user, laboratory information associated with the patient user, and biometric data associated with the patient user.

4. The method of claim 3, further comprising:
    accessing a health monitoring device associated with the patient user; and
    receiving the biometric data associated with the patient user from the health monitoring device.

5. The method of claim 1, wherein the outreach parameter corresponds to a social condition or a medication adherence condition.

6. The method of claim 1, wherein the aggregate data record comprises one or more conditions associated with the patient user, the method further comprising:
    displaying the aggregate data record on a graphical user interface, wherein the graphical user interface includes a patient information region and a condition related region, the patient information region comprising a first plurality of fields that identify the patient user, the condition related region comprising a second plurality of fields associated with the one or more conditions.

7. The method of claim 1, further comprising:
    obtaining a list of medical entries associated with the patient user;
    determining that a particular medical entry of the list of medical entries satisfies the outreach parameter; and automatically highlighting the particular medical entry in the list of medical entries that has been determined to satisfy the outreach parameter.

8. The method of claim 7, wherein the medical entry comprises medication previously prescribed to the patient user, and wherein the outreach parameter corresponds to a measure of how late the patient user was at re-filling a medication represented by the particular medical entry.

9. The method of claim 1, further comprising:
generating status information in the aggregate data record, the status information corresponding to the outreach event.

10. The method of claim 9, further comprising:
tracking the status information to establish a relationship between the subset of data records and the outreach parameter.

11. The method of claim 9, further comprising:
receiving an update from the second computer device after a second user of the second computer device contacts the patient user; and
storing the update in the status information.

12. The method of claim 9, further comprising:
receiving input from the first computer device, the input comprising a reason for connecting with the patient user; and
generating a communication that is presented to the second computer device, the communication identifying the patient user and the reason for connecting with the patient user, wherein the reason comprises provision of at least one of healthcare support, pharmaceutical support, medicine disposal equipment, or a remote monitoring device.

13. The method of claim 11, wherein a first user of the first computer device is associated with a first organization, and wherein the second user of the second computer device is associated with a second organization.

14. The method of claim 12, further comprising:
receiving a request from the second computer device to route the communication to a third computer device; and
in response to receiving the request from the second computer device to route the communication to the third computer device, replacing the viewing-level access associated with the second computer device with the restricted-level access, and associating the third computer device with the viewing-level access while continuing to the first computer device with the viewing-level access.

15. The method of claim 13, wherein the secure healthcare communication exchange platform is accessible by the first and second users via a website.

16. The method of claim 10, wherein tracking the status information to establish the relationship between the subset of data records and the outreach parameter comprises determining after a given time interval that the subset of data records no longer satisfies the outreach parameter.

17. The method of claim 1, further comprising:
storing a plurality of collections of data records, the plurality of the collections of data records corresponding to a plurality of entities comprising the patient user,
searching the plurality of collections of data records based on one or more criteria to identify a second subset of data records that include one or more conditions that satisfy the outreach parameter; and
selecting the collection of data records associated with the patient user from the subset of data records.

18. The method of claim 1, further comprising causing presentation of a plurality of status information corresponding to a plurality of outreach events.

19. A system comprising:
one or more processors coupled to a memory comprising non-transitory computer instructions that when executed by the one or more processors perform operations comprising:
accessing, from a secure healthcare communication exchange platform, a collection of data records from a plurality of data sources, the collection of data records corresponding to a patient user;
modifying each data record in the collection of data records, the modification comprising tagging each data record with a unique identifier value;
generating, based on the unique identifier value associated with each record in the collection of data records, an aggregate data record associated with the patient user;
receiving a first selection from a graphical user interface of a first computer device, the first selection corresponding to an adherence metric associated with the aggregate data record;
in response to the first selection, analyzing the adherence metric using a convolutional neural network trained to generate a prediction on a statistical measure of adherence of the adherence metric;
based on the generated prediction, automatically identifying, using a machine learning technique, a subset of data records of the aggregate data record that satisfies an outreach parameter, the machine learning technique trained to analyze the aggregate data record;
in response to determining that the subset of data records satisfy the outreach parameter, receiving a second selection from a graphical user interface by the first computer device, the first selection triggering an outreach event to authorize a second computer device to access the aggregate data record, wherein the first computer device has a viewing-level access authorizing the first computer device to view the aggregate data record, and the second computer device user has a restricted-level access that restricts the second computer device from viewing the aggregate data record;
in response to triggering the outreach event,
automatically modifying, without user intervention the restricted-level access associated with the second computer device to the viewing-level access, the second computer device becoming authorized to view the aggregate data record; and
in response to the second computer device becoming authorized to view the aggregate data record, initiating contact through the secure healthcare communication exchange platform with the patient user so that a health condition associated with the patient user is resolved and the aggregate data record associated with the patient user is exposed only to an authorized user.

20. A non-transitory computer readable medium comprising non-transitory computer-readable instructions for performing operations comprising:
accessing, from a secure healthcare communication exchange platform, a collection of data records from a plurality of data sources, the collection of data records corresponding to a patient user;
modifying each data record in the collection of data records, the modification comprising tagging each data record with a unique identifier value;

generating, based on the unique identifier value associated with each record in the collection of data records, an aggregate data record associated with the patient user;

receiving a first selection from a graphical user interface of a first computer device, the first selection corresponding to an adherence metric associated with the aggregate data record;

in response to the first selection, analyzing the adherence metric using a convolutional neural network trained to generate a prediction on a statistical measure of adherence of the adherence metric;

based on the generated prediction, automatically identifying, using a machine learning technique, a subset of data records of the aggregate data record that satisfies an outreach parameter, the machine learning technique trained to analyze the aggregate data record;

in response to determining that the subset of data records satisfy the outreach parameter, receiving a second selection from a graphical user interface by the first computer device, the first selection triggering an outreach event to authorize a second computer device to access the aggregate data record, wherein the first computer device has a viewing-level access authorizing the first computer device to view the aggregate data record, and the second computer device has a restricted-level access that restricts the second computer device from viewing the aggregate data record;

in response to triggering the outreach event,
automatically modifying, without user intervention the restricted-level access associated with the second computer device to the viewing-level access, the second computer device becoming authorized to view the aggregate data record; and in response to the second computer device becoming authorized to view the aggregate data record, initiating contact through the secure healthcare communication exchange platform with the patient user so that a health condition associated with the patient user is resolved and the aggregate data record associated with the patient user is exposed only to an authorized user.

\* \* \* \* \*